United States Patent
Dickhaut et al.

(10) Patent No.: US 9,975,895 B2
(45) Date of Patent: May 22, 2018

(54) SUBSTITUTED PYRIMIDINIUM COMPOUNDS AND DERIVATIVES FOR COMBATING ANIMAL PESTS

(71) Applicant: BASF SE, Ludwigshafen (DE)

(72) Inventors: Joachim Dickhaut, Heidelberg (DE);
Arun Narine, Mannheim (DE);
Swetlana Derksen, Mannheim (DE);
Nina Gertrud Bandur, Ludwigshafen (DE); Wolfgang Von Deyn, Neustadt (DE); Raffael Koller, Mannheim (DE);
Jean-Yves Wach, Mannheim (DE);
Juergen Langewald, Mannheim (DE);
Nancy B. Rankl, Cary, MA (US)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 14/898,892

(22) PCT Filed: Jun. 17, 2014

(86) PCT No.: PCT/EP2014/062687
§ 371 (c)(1),
(2) Date: Dec. 16, 2015

(87) PCT Pub. No.: WO2014/202582
PCT Pub. Date: Dec. 24, 2014

(65) Prior Publication Data
US 2016/0122351 A1    May 5, 2016

Related U.S. Application Data

(60) Provisional application No. 61/835,659, filed on Jun. 17, 2013.

(51) Int. Cl.
C07D 471/16    (2006.01)
A01N 43/90    (2006.01)
C07D 471/14    (2006.01)

(52) U.S. Cl.
CPC ........... *C07D 471/16* (2013.01); *A01N 43/90* (2013.01); *C07D 471/14* (2013.01)

(58) Field of Classification Search
None
See application file for complete search history.

(56) References Cited

FOREIGN PATENT DOCUMENTS

| WO | WO 2009099929 | 8/2009 |
|---|---|---|
| WO | WO 2011017342 | 2/2011 |
| WO | WO 2011017347 | 2/2011 |
| WO | WO 2012090514 | 7/2012 |
| WO | WO 2012136724 | 10/2012 |
| WO | WO 2014167084 | 10/2014 |

OTHER PUBLICATIONS

International Search Report, issued in PCT/EP2014/062687, dated Aug. 7, 2014.
Bitter and Pete, "Nitrogen Bridgehead Compounds. Part 56. Reaction of 2,6a-Diaza-3a-Azoniaphenalene Quaternary Salts with N-Nucleophiles and Carbanions," Heterocycles, vol. 23, No. 10, (1985), pp. 2549-2556.
Kafka, "Synthesis of Highly Symmetric Mesomeric Triazaphenalene Betaines," J. Heterocyclic Chem., vol. 41, (2004), pp. 717-721.
Stadlbauer et al., "Mesoionische Sechsringheterocyclen, XVI Synthese von 2a,5a-Diaza-acenaphthylen Mesoionen," Monatshefie für Chemie, vol. 114, (1983), pp. 965-972.
International Preliminary Report on Patentability, issued in PCT/EP2014/062687, dated Dec. 17, 2015.

*Primary Examiner* — John Pak
*Assistant Examiner* — Daniel L Branson
(74) *Attorney, Agent, or Firm* — Brinks Gilson & Lione

(57) ABSTRACT

Substituted pyrimidinium compounds of the general formula (I) and their uses for combating animal pests
The present invention relates to substituted pyrimidinium compounds of formula (I), to the stereoisomers, salts, tautomers and N-oxides thereof and to compositions comprising such compounds. The invention also relates to methods and uses of these substituted pyrimidinium compounds and of compositions thereof, for combating and controlling animal pests. Furthermore the invention relates also to pesticidal methods of applying such substituted pyrimidinium compounds.
The substituted pyrimidinium compounds of the present invention are defined by the following general formula (I):

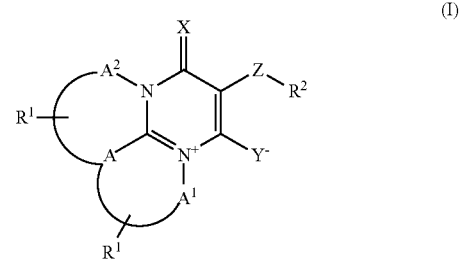

wherein X, Y, Z, $R^1$, $R^2$, A, $A^1$ and $A^2$ are defined as in the description.

21 Claims, No Drawings

SUBSTITUTED PYRIMIDINIUM COMPOUNDS AND DERIVATIVES FOR COMBATING ANIMAL PESTS

This application is a National Stage application of International Application No. PCT/EP2014/062687, filed Jun. 17, 2014, which claims the benefit of U.S. Provisional Application No. 61/835,659, filed Jun. 17, 2013.

The present invention relates to insecticidal substituted pyrimidinium compounds and/or to the compositions comprising such compounds for combating invertebrate pests. The invention also relates to pesticidal methods, to uses and to applications of substituted pyrimidinium compounds as described in the present invention and the stereoisomers, salts, tautomers and N-oxides thereof as well as compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

It has been found that these objectives can be achieved by substituted pyrimidinium compounds of the general formula (I), as defined below, including their stereoisomers, their salts, in particular their agriculturally or veterinary acceptable salts, their tautomers and their N-oxides.

Therefore, in a first aspect the present invention relates to substituted pyrimidinium compounds of formula (I) or a composition comprising at least one compound of formula (I):

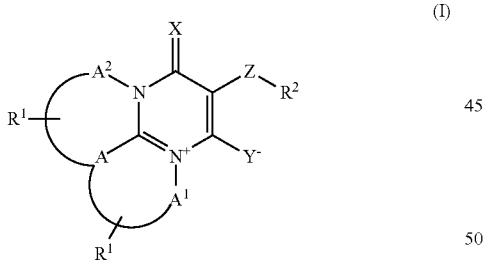

(I)

wherein

X, Y are each independently O or S;

Z is a direct bond, O, $S(O)_m$, $NR^b$, $C(R^aR^{aa})O$, $C(=X^1)$, $C(=X^1)Y^1$, or $Y^1C(=X^1)$;

$X^1$ is O, S, or $NR^b$;

$Y^1$ is O, S, or $NR^c$;

A is C or N and, wherein the two nitrogens of the pyrimidinium ring taken together with the contiguous linking carbon atom and with A, $A^1$, and $A^2$ as depicted in formula (I), form an eight- to fourteen-membered bicyclic rings system which is substituted by at least one $R^1$ being not H, and wherein each remaining ring member of the bicyclic rings system is selected from carbon atoms and up to 4 heteroatoms independently selected from up to 2O, up to 2S, and up to 3 $N(R^c)_p$ in each ring, wherein the sulfur atom ring members are independently selected from $S(=O)_m$, wherein each ring may be partially or fully substituted by $R^1$; or two geminally bound groups $R^1$ together may form a group selected from =O, =S, $=CR^bR^c$, $=NR^c$, $=NOR^c$, and $=NNR^cR^c$;

$A^1$, $A^2$ are each independently C, $CR^1$, O, S, or $NR^1$, with the proviso that $R^1$ is not halogen or CN in $NR^1$;

$R^1$ is each independently H, halogen, CN, $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, wherein the aforementioned groups may be unsubstituted, partially, or fully substituted with $R^a$, or $R^1$ may form a carbo- or heterocyclic three- to ten-membered ring or a seven- to eleven-membered rings system, which ring or rings system may be saturated, partially unsaturated, or aromatic, and which ring or rings system may contain 1 to 4 heteroatoms selected from $N(R^c)_p$, O, and S, wherein S may be oxidized, and wherein the carbo- or heterocyclic ring or rings system may be unsubstituted, partially, or fully substituted by $R^a$;

$R^a$ is each independently halogen, $C_1$-$C_6$-alkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, $N=S(=O)_pR^cR^c$, or a three- to six-membered saturated, or partially unsaturated or aromatic carbo- or heterocyclic ring, which may contain 1 to 3 heteroatoms selected from $N-(R^c)_p$, O, and S, wherein S may be oxidized, and wherein the aforementioned groups and the carbo- or heterocyclic ring may be partially or fully substituted by $R^{1aa}$; or two geminally bound groups $R^a$ together may form a group selected from =O, =S, $=CR^bR^c$, $=NR^c$, $=NOR^c$, and $=NNR^cR^c$;

$R^{1aa}$ is each independently halogen, $C_1$-$C_6$-alkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^e$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^{1aa}$ together may form a group selected from =O, =S, $=CR^bR^c$, $=NR^c$, $=NOR^c$, and $=NNR^cR^c$;

$X^2$ is independently O or S;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy or a three- to six-membered saturated, or partially unsaturated or aromatic carbo- or heterocyclic ring, which may contain 1 to 3 heteroatoms selected from $N(R^c)_p$, O, and S, wherein S may be oxidized and which carbo- or heterocyclic ring may be partially or fully substituted by $R^{aa}$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^c$ is each independently hydrogen, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted by $R^{aa}$;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted by $R^3$;

$R^d$ is each independently hydrogen, phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, wherein the above mentioned groups may be substituted by one or more halogen;

$R^e$ is each independently, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted by $R^{aa}$;

n is 0, 1 or 2;

m is 0, 1, or 2;

p is 0 or 1;

$R^2$ is H, halogen, CN, $C_1$-$C_8$ alkyl, $C_2$-$C_8$ alkenyl, $C_2$-$C_8$ alkynyl, $C_3$-$C_{10}$ cycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, or $C_3$-$C_6$ cycloalkenyl, wherein the aforementioned groups may be unsubstituted, partially, or fully substituted with $R^{2a}$, or $R^2$ may form a carbo- or heterocyclic three- to ten-membered ring or a seven- to eleven-membered rings system, which ring or rings system may be saturated, partially unsaturated, or aromatic, and which ring or rings system may contain 1 to 4 heteroatoms selected from $N(R^c)_p$, O, and S, wherein S may be oxidized, and wherein the carbo- or heterocyclic ring or rings system may be unsubstituted, partially, or fully substituted by $R^{2a}$;

with the proviso that if $R^2$ is halogen or CN, then Z is a direct bond;

$R^{2a}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^e$, $OC(=O)NR^bR^e$, $NR^bC(=O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^b—SO_2NR^bR^c$, $N=S(=O)_pR^cR^c$, or a three- to six-membered saturated, or partially unsaturated or aromatic carbo- or heterocyclic ring, which may contain 1 to 3 heteroatoms selected from $N—(R^c)_p$, O, and S, wherein S may be oxidized, and wherein the aforementioned groups and the carbo- or heterocyclic ring may be partially or fully substituted by $R^{2aa}$; or two geminally bound groups $R^{2a}$ together may form a group selected from =O, =S, $=CR^bR^c$, $=NR^c$, $=NOR^c$, and $=NNR^cR^c$;

$R^{2aa}$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^e$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^{2aa}$ together may form a group selected from =O, =S, $=CR^bR^c$, $=NR^c$, $=NOR^c$, and $=NNR^cR^c$;

$R^3$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^e$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, or $N=S(=O)_pR^cR^c$, or two geminally bound groups $R^3$ together may form a group selected from =O, =S, $=CR^bR^c$, $=NR^c$, $=NOR^c$, and $=NNR^cR^c$;

and/or stereoisomer or agriculturally or veterinary acceptable salts or tautomers or N-oxides thereof.

The substituted pyrimidinium compounds of the formula (I), and their agriculturally acceptable salts are highly active against animal pest, i.e. harmful arthropodes and nematodes, especially against difficult to control insects and acaridae.

Moreover, the present invention relates to and includes the following embodiments:

composition comprising at least one compound of formula (I) as defined above;

agricultural and veterinary compositions comprising an amount of at least one compound of formula (I) or an enantiomer, diasteromer or salt thereof as defined above;

method for combating invertebrate pests, infestation, or infection by invertebrate pests, which method comprises contacting said pest or its food supply, habitat or breeding grounds with a pesticidally effective amount of at least one compound of formula (I) as defined above or a composition thereof;

method for controlling invertebrate pests, infestation, or infection by invertebrate pests, which method comprises contacting said pest or its food supply, habitat or breeding grounds with a pesticidally effective amount of at least one compound of formula (I) as defined above or a composition comprising at least one compound of formula (I);

method for preventing or protecting against invertebrate pests comprising contacting the invertebrate pests, or their food supply, habitat or breeding grounds with a substituted pyrimidinium compounds of the general formula (I) as defined above or a composition comprising at least one compound of formula (I) as defined above or a composition comprising at least one compound of formula (I);

a method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

a non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or a composition comprising at least one compound of formula (I);

a method for treating, controlling, preventing or protecting animals against infestation or infection by parasites by administering or applying orally, topically or parenterally to the animals a substituted pyrimidinium compound of the general formula (I) as defined above or a composition comprising at least one compound of formula (I);

seed comprising a compound of formula (I) as defined above, in an amount of from 0.1 g to 10 kg per 100 kg of seed;

the use of the compounds of formula (I) as defined above for protecting growing plants or plant propagation material from attack or infestation by invertebrate pests; the use of compounds of formula (I) or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of an compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of the present invention including if applicable their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound as disclosed in the present invention, for combating or controlling invertebrate pests, in particular invertebrate pests of the group of insects, arachnids and nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I).

The term "composition(s) according to the invention" or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The substituted pyrimidinium compounds of formula (I) according to the present invention have not yet been described for pesticidal uses or pesticidal applications in agricultural industry or veterinary practice.

Heterocyclic substituted pyridinium derivatives and their use as pesticides have been disclosed in WO 2009099929 as well as in WO 2011017347 and in WO 2011017342.

Tricyclic pyrimidinium derivatives which are substituted on the pyrimidinium ring have also been described in Monatshefte für Chemie 114 (1983), 965-972.

However, the particularly substituted pyrimidinium compounds of formula (I) with the characteristic substitution pattern as defined in the present invention have not yet been described.

Depending on the substitution pattern, the compounds of the formula (I) may have one or more centers of chirality, in which case they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures.

Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

Depending on the substitution pattern, the compounds of the formulae (I) may be present in the form of their tautomers. Hence the invention also relates to the tautomers of the formula (I) and the stereoisomers, salts, tautomers and N-oxides of said tautomers.

The compounds of the present invention may be amorphous or may exist in one or more different crystalline states (polymorphs) or modifications which may have a different macroscopic properties such as stability or show different biological properties such as activities.

The present invention includes both amorphous and crystalline compounds of the formula (I), mixtures of different crystalline states or modifications of the respective compound (I), as well as amorphous or crystalline salts thereof.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae (I) with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chloro-fluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$- haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as subsitituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cyclo-heptyl, cyclooctyl and cyclodecyl.

The term "alkylcycloalkyl" denotes as well as the term "alkyl which may be substituted by cycloalkyl" an alkyl group which is substituted by a cycloalkyl ring, wherein alkyl and cycloakyl are as herein defined.

The term "cycloalkylalkyl" denotes as well as the term "cycloalkyl which may be substituted by alkyl" a cycloalkyl ring which is substituted by an alkyl group, wherein alkyl and cycloakyl are as herein defined.

The term "alkylcycloalkylalkyl" denotes as well as the term "alkylcycloalkyl which may be substituted by alkyl" an alkylcycloalkyl group which is substituted by an alkyl, wherein alkyl and alkylcycloakyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted by cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1,1'-bicyclopropyl-2-yl and (1R,2R)-1,1'-bicyclopropyl-2-yl.

The term "3- to 6-membered carbocyclic ring" as used herein refers to cyclopropane, cyclo-butane, cyclopentane and cyclohexane rings.

The term "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, $—CH(CH_3)—$, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Embodiments and preferred compounds of the present invention for use in pesticidal methods and for insecticidal application purposes are outlined in the following paragraphs.

The remarks made below concerning preferred embodiments of the variables (substituents) of the compounds according to the invention, especially with respect to their substituents X, Y, Z, $X^1$, $X^2$, $Y^1$, A, $A^1$, $A^2$, $R^1$, $R^a$, $R^{1aa}$, $R^{aa}$, $R^b$, $R^c$, $R^d$, $R^e$, $R^2$, $R^{2a}$, $R^{2aa}$, $R^3$, m, n, and p are valid both on their own and, in particular, in every possible combination with each other and where applicable, the uses, the methods and the compositions according to the invention.

In a particular embodiment, the variables of the compounds of formula (I) have the following meanings, these meanings, both on their own and in combination with one another, being particular embodiments of the compounds of the formula (I).

In one preferred embodiment of the compounds of formula (I), X is O. These compounds correspond to the compounds of formula (I.1).

In a further embodiment of the compounds of the formula (I), X is S. These compounds correspond to the compounds of formula (I.2).

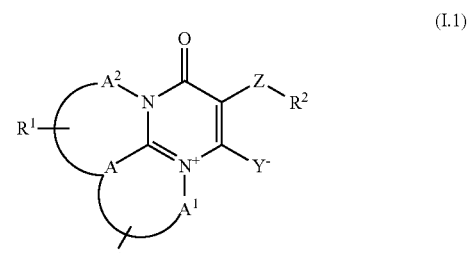

(I.1)

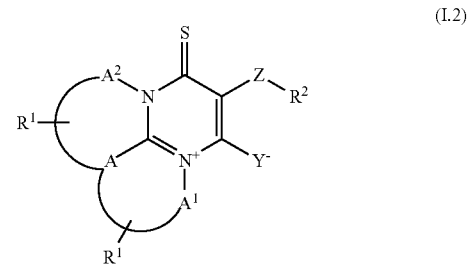

(I.2)

In another embodiment of the compounds of formula (I), Y is S. These compounds correspond to the compounds of formula (I.A).

In another embodiment of the compounds of formula (I), Y is O. These compounds correspond to the compounds of formula (I.B).

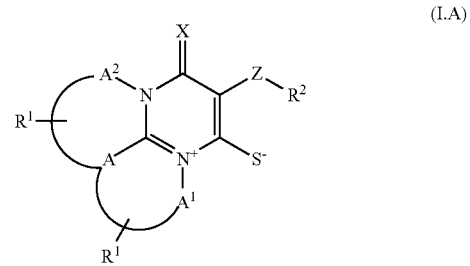

(I.A)

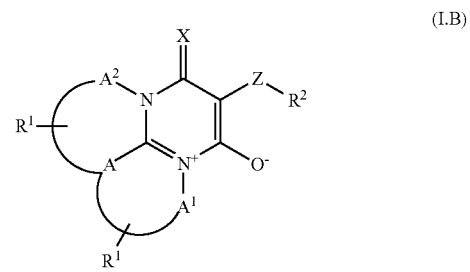

(I.B)

In another embodiment of the compounds of formula (I), Y is S and X is O. These compounds correspond to compounds of formula I.1.A:

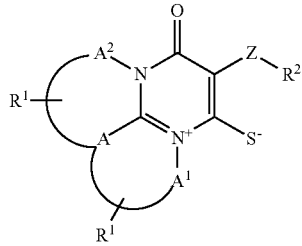

(I.1.A)

In another embodiment of the compounds of formula (I), Y is S and X is S. These compounds correspond to compounds of formula I.2.A.

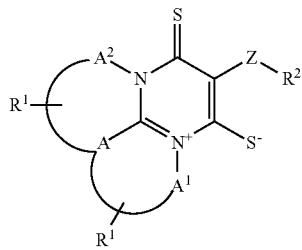

(I.2.A)

In another embodiment of the compounds of formula (I), Y is O and X is O. These compounds correspond to compounds of formula I.1.B.

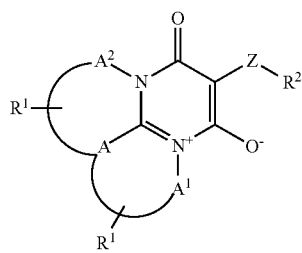

(I.1.B)

In another embodiment of the compounds of formula (I), Y is O and X is S. These compounds correspond to compounds of formula I.2.B.

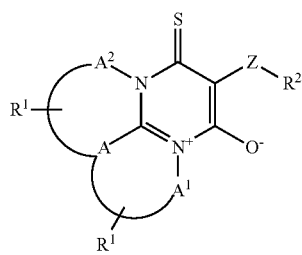

(I.2.B)

Within these embodiments, compounds of formula I.1.B are preferred.

In an embodiment of the compounds of formula (I), Z is a direct bond or $C(R^a R^{aa})O$.

In a further embodiment of the compounds of formula (I), Z is a direct bond.

In an embodiment of the compounds of formula (I), Z is O, $S(O)_m$, $NR^b$, $C(=X^1)$, $C(=X^1)Y^1$, or $Y^1C(=X^1)$. In a further embodiment, Z is O, $S(O)_m$, or $NR^b$. In another embodiment, Z is $C(=X^1)$, $C(=X^1)Y^1$, or $Y^1C(=X^1)$.

In an embodiment of the compounds of formula (I), $X^1$ is O.

In an embodiment of the compounds of formula (I), $X^1$ is S.

In an embodiment of the compounds of formula (I), $X^1$ is $NR^b$.

In an embodiment of the compounds of formula (I), $Y^1$ is O.

In an embodiment of the compounds of formula (I), $Y^1$ is S.

In an embodiment of the compounds of formula (I), $Y^1$ is $NR^c$.

In an embodiment of the compounds of formula (I), A is C or N and, wherein the two nitrogens of the pyrimidinium ring taken together with the contiguous linking carbon atom and with A, $A^1$, and $A^2$ as depicted in formula (I), form a twelve- to thirteen-membered bicyclic rings system which is substituted by at least one $R^1$ being not H, and wherein each remaining ring member of the bicyclic rings system is selected from carbon atoms and up to 4 heteroatoms independently selected from up to 2O, up to 2S, and up to 3 $N(R^c)_p$ in each ring, wherein the sulfur atom ring members are independently selected from $S(=O)_m$, wherein each ring may be partially or fully substituted by $R^1$; wherein $R^1$, $A^1$ and $A^2$ have the meaning as hereunder described.

In a further embodiment of the compounds of formula (I), A is C, and wherein the two nitrogens of the pyrimidinium ring taken together with the contiguous linking carbon atom and with A, $A^1$, and $A^2$ as depicted in formula (I), form a five and six-membered bicyclic rings system which is substituted by at least one $R^1$ being not H, and wherein each remaining ring member of the bicyclic rings system are carbon atoms, wherein each ring may be partially or fully substituted by $R^1$.

In a further embodiment of the compounds of formula (I), A is C, and wherein the two nitrogens of the pyrimidinium ring taken together with the contiguous linking carbon atom and with A, $A^1$, and $A^2$ as depicted in formula (I), form a six and six-membered bicyclic rings system which is substituted by at least one $R^1$ being not H, and wherein each remaining ring member of the bicyclic rings system are carbon atoms, wherein each ring may be partially or fully substituted by $R^1$.

In an embodiment, $A^1$, $A^2$ are each independently C or $CR^1$.

In a preferred embodiment, A or $A^2$ is $CR^1$.

In a further embodiment, A is C, and wherein the two nitrogens of the pyrimidinium ring taken together with the contiguous linking carbon atom and with A, $A^1$, and $A^2$ as depicted in formula (I), form a bicyclic rings system which is substituted by at least one $R^1$ being not H, resulting in the compounds of formula (II) selected from the group of compounds of formulae II-1 to II-7:

(II-1)
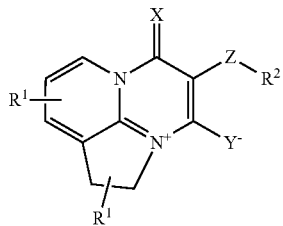

(II-2)
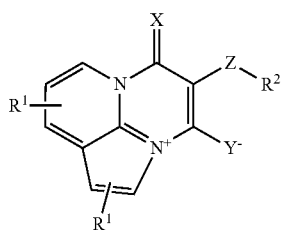

(II-3)
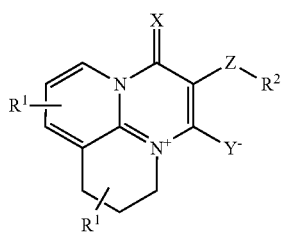

(II-4)
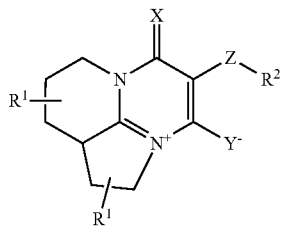

(II-5)
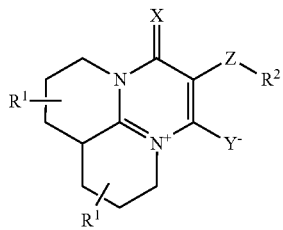

(II-6)
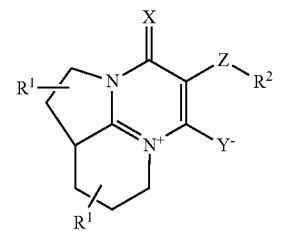

(II-7)
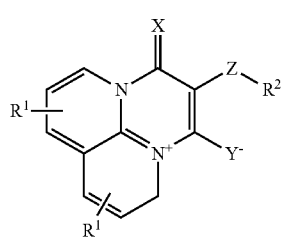

In a further embodiment, compounds of formula (I) are selected from the group of compounds of formulae II-1, II-2, II-3, and II-7.

In a further embodiment, compounds of formula (I) are selected from the group of compounds of formulae II-1, II-2 and II-3.

In a further embodiment, compounds of formula (I) is a compound of formula II-1 or II-2.

In another embodiment, compound of formula (I) is a compound of formula II1 to II-7, wherein at least one $R^1$ being not hydrogen is the substituent of the carbon atom adjacent to one nitrogen of the pyrimidinium ring In an embodiment, $R^1$ is hydrogen, $C_1$-$C_8$-alkyl, $C_2$-$C_8$-alkenyl, $C_2$-$C_8$-alkynyl, $C_1$-$C_6$-alkoxy, $C_3$-$C_6$-cycloalkyl, $C_4$-$C_{10}$-cycloalkenyl or $C_5$-$C_{11}$-cycloalkylcycloalkyl, wherein the C-atoms of the aforementioned groups may be unsubstituted, or partially or fully substituted by $R^a$, wherein $R^a$ has the meaning as hereunder described.

In another embodiment, $R^1$ is a three- to ten-membered saturated, or partially saturated or heterocyclic ring system, which may contain 1 to 3 heteroatoms selected from $N(R^c)_p$, O, and S, wherein S may be oxidized and which heterocyclic ring may be unsubstituted or substituted by $R^a$.

In a further embodiment, $R^1$ is hydrogen, $C_1$-$C_4$-alkyl, $C_2$-$C_8$-alkenyl, $C_1$-$C_6$-alkoxy, $C_3$-$C_6$-cycloalkyl or $C_5$-$C_{11}$-cycloalkylcycloalkyl, wherein the C-atoms of the aforementioned groups may be unsubstituted, or partially or fully substituted by halogen.

In an embodiment, $R^1$ is $C_1$-$C_4$-haloalkyl, $C_1$-$C_6$-alkoxy, or a five- or six-membered saturated, partially unsaturated or aromatic carbo- or heterocyclic ring, which ring may contain 1 to 2 heteroatoms independently selected from $N(R^c)_p$, O and S, and wherein the aforementioned groups may be substituted with up to 2 $R^a$.

In a further embodiment, $R^1$ is five- or six-membered saturated, partially unsaturated or aromatic heterocyclic ring, which ring may contain 1 to 2 heteroatoms independently selected from $N(R^c)_p$, or S, and wherein the heterocyclic ring may be substituted with up to 2 $R^a$.

In an embodiment $R^1$ is a five-membered aromatic heterocyclic ring, which contains 2 heteroatoms independently selected from $N(R^c)_p$, O and S, wherein the heterocyclic ring is substituted by $(R^a)_n$.

In an embodiment $R^1$ is a five-membered unsaturated heterocyclic ring, which contains 2 heteroatom independently selected from $N(R^c)_p$, O and S, preferably selected from N and S, and wherein the heterocyclic ring is substituted by $(R^a)_n$.

In an embodiment $R^1$ is a six-membered aromatic heterocyclic ring, which contains 2 heteroatoms independently selected from $N(R^c)_p$, O and S, preferably being N, and wherein the heterocyclic ring is substituted by $(R^a)_n$.

In an embodiment $R^1$ is a six-membered aromatic heterocyclic ring, which contains 1 heteroatom selected from N(R$^c$)$_p$, O and S, preferably being N, and wherein the heterocyclic ring is substituted by (R$^a$)$_n$.

In an embodiment R$^1$ is pyridyl which is substituted by (R$^a$)$_n$.

In an embodiment R$^1$ is pyrimidyl.

In an embodiment R$^1$ is thiazolyl which is substituted by (R$^a$)$_n$.

In another embodiment, R$^1$ is selected from any one of the following ring systems D-1 to D-55:

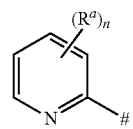
D-1

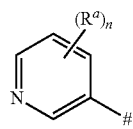
D-2

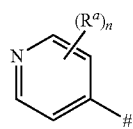
D-3

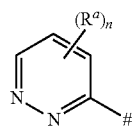
D-4

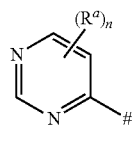
D-5

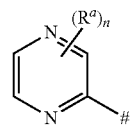
D-6

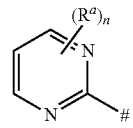
D-7

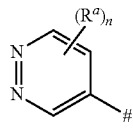
D-8

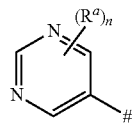
D-9

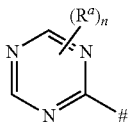
D-10

-continued

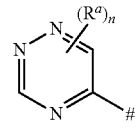
D-11

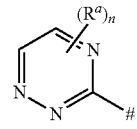
D-12

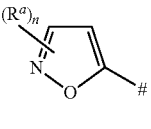
D-13

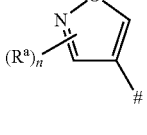
D-14

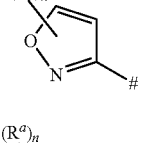
D-15

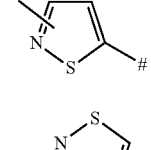
D-16

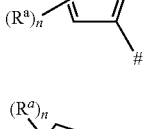
D-17

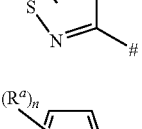
D-18

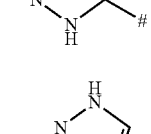
D-19

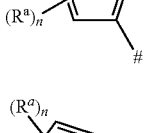
D-20

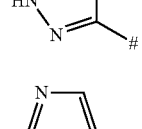
D-21

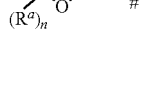
D-22

-continued
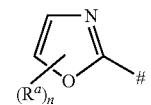 D-23
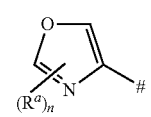 D-24
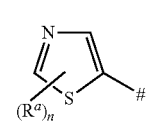 D-25
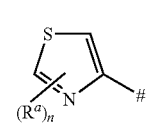 D-26
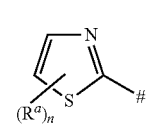 D-27
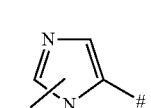 D-28
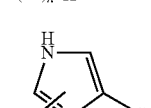 D-29
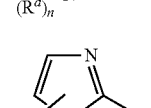 D-30
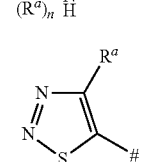 D-31
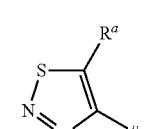 D-32
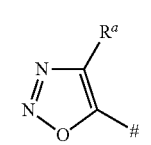 D-33
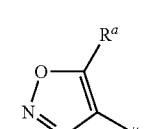 D-34
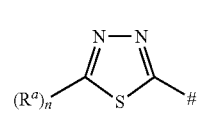 D-35
-continued
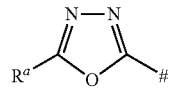 D-36
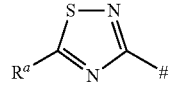 D-37
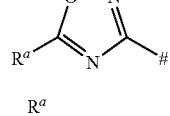 D-38
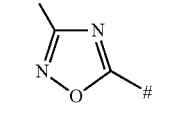 D-39
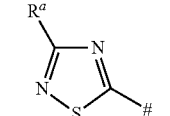 D-40
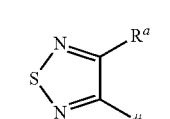 D-41
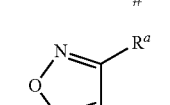 D-42
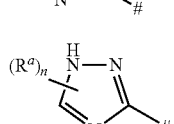 D-43
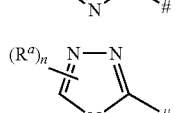 D-44
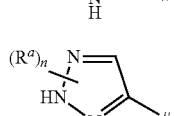 D-45
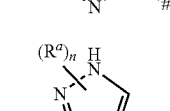 D-46
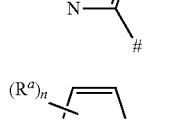 D-47
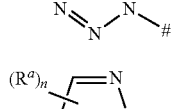 D-48
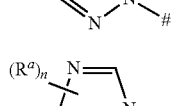 D-49

-continued
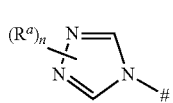 D-50
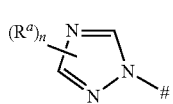 D-51
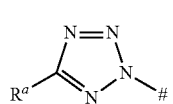 D-52
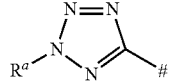 D-53
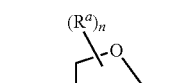 D-54
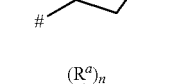 D-55
Wherever used in a structure, the following: # denotes the bond to the core structure of formula (I).
In a further embodiment $R^1$ is selected from any one of the following ring systems:
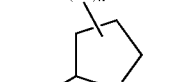 D-1
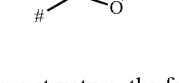 D-2
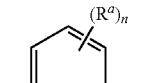 D-3
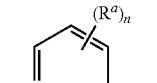 D-5
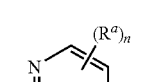 D-6
-continued
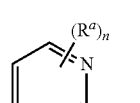 D-7
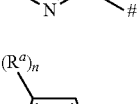 D-16
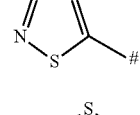 D-17
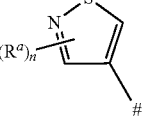 D-20
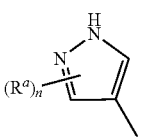 D-22
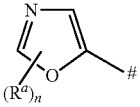 D-23
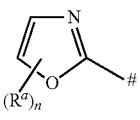 D-24
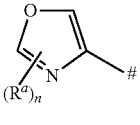 D-25
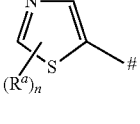 D-26
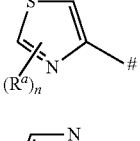 D-27
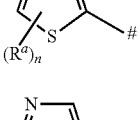 D-28
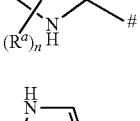 D-29

-continued

D-30
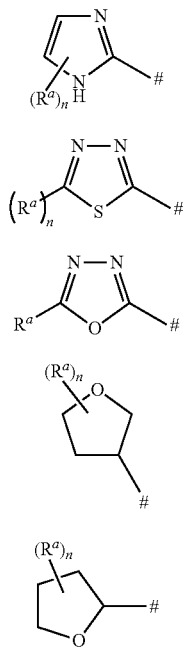

D-35

D-36

D-54

D-55

In a further embodiment, R¹ is selected from the following rings systems D-2, D-9, D-13, D-17, D-22, D-25, D-28, D-29 and D-54:

D-2
D-9
D-13
D-17
D-22
D-25
D-28

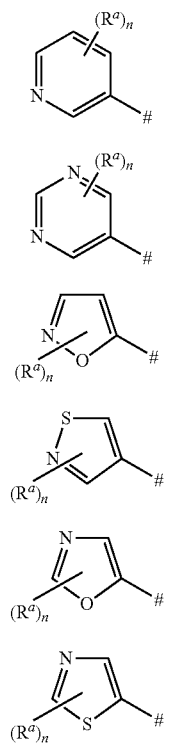

-continued

D-29
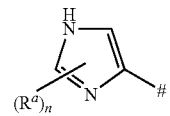

D-54
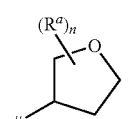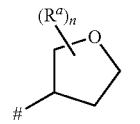

In a further embodiment, R¹ is selected from the following rings systems D-2, D-9, D-22, D-25, D-28, D-29 and D-54:

D-2
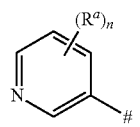

D-9
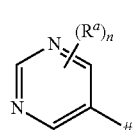

D-22
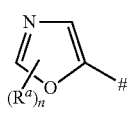

D-25
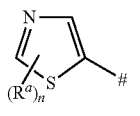

D-28
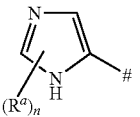

D-29
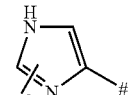

D-54
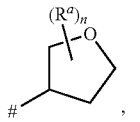, wherein $R^a$ is halogen, $C_1$-$C_4$-haloalkyl or $C_1$-$C_4$-alkylthio; preferably $R^a$ is halogen or halomethyl.

In a further embodiment, R¹ is selected from the following rings systems D-2, D-9 and D-25:

D-2
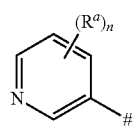

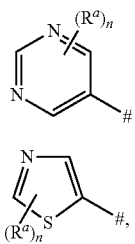

D-9

D-25 wherein $R^a$ is halogen or $C_1$-$C_4$-haloalkyl; preferably $R^a$ is Cl, Br, F or $CF_3$, most preferably $R^a$ is Cl or $CF_3$.

In a further embodiment $R^1$ is selected from the following rings systems D-2, D-25 or D-54:

D-2

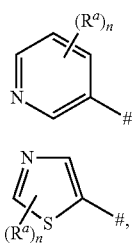

D-9

D-25 wherein $R^a$ is halogen or $C_1$-$C_4$-haloalkyl; preferably $R^a$ is Cl, Br, F or $CF_3$, most preferably $R^a$ is Cl or $CF_3$.

In a further embodiment, $R^1$ is selected from the following rings systems D-2 and D-25:

D-2

D-25 wherein $R^a$ is halogen or $C_1$-$C_4$-haloalkyl; preferably $R^a$ is Cl, Br, F or $CF_3$, most preferably $R^a$ is Cl or $CF_3$.

In another embodiment $R^1$ is selected from the following rings systems D-2a, D-2b, D-2c, D-9a, D-9b, D-25a and D-54a:

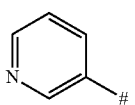

D-2a

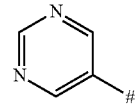

D-9b

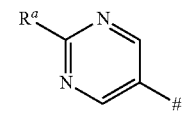

D-9a

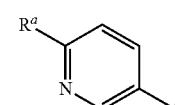

D-2b

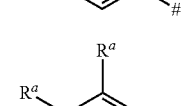

D-2c

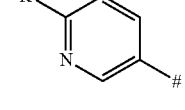

D-25a

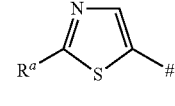

D-54a wherein $R^a$ are independently from each other selected from Cl, Br, F and $CF_3$.

In another embodiment $R^1$ is selected from the following rings systems D-2a, D-2b, D-2c, D-9a, D-9b, and D-25a.

In another embodiment $R^1$ is selected from the following rings systems D-2b, D-9b, and D-25a.

In another embodiment $R^1$ is D-2, preferably D-2b or D-2c, particularly D-2b, wherein $R^a$ is Cl or $CF_3$. In a further embodiment $R^1$ is D-2a.

In another embodiment, $R^1$ is D-25, preferably D-25a substituted by Cl.

In another embodiment, $R^1$ is D-9, preferably D-9b. In another embodiment $R^1$ is $C_1$-$C_4$-alkyl, $C_2$-$C_8$-alkenyl, $C_3$-$C_6$-cycloalkyl or phenyl, wherein the C-atoms of the aforementioned groups may be unsubstituted, or partially or fully substituted by $R^a$, wherein $R^a$ has the meaning as hereunder described.

In a further embodiment $R^1$ is $C_1$-$C_4$-alkyl, $C_3$-$C_6$-cycloalkyl or phenyl, wherein the C-atoms of the aforementioned groups may be unsubstituted, or partially or fully substituted by halogen or $C_1$-$C_4$-alkyl.

In a further embodiment $R^1$ is $C_1$-$C_4$-alkyl, $C_3$-$C_6$-cycloalkyl or phenyl, wherein the C-atoms of the aforementioned groups are partially or fully substituted by halogen; preferably $R^1$ is methyl, ethyl, isopropyl, cyclopropyl or phenyl, and which groups are substituted by at least one halogen.

In another embodiment $R^1$ is $C_1$-$C_4$-alkyl, $C_3$-$C_6$-cycloalkyl or phenyl, preferably $CH_3$, $CH_2CH_3$, $CH(CH_3)_2$, cyclopropyl or phenyl.

In an embodiment, $R^2$ is hydrogen, halogen, CN, $NO_2$, $C_1$-$C_6$-alkyl, $C_1$-$C_6$-haloalkyl, $C_1$-$C_6$-haloalkoxy, $C_1$-$C_6$-alkoxy, $C_2$-$C_6$-alkenyl, $C_2$-$C_6$-alkynyl, $C_3$-$C_6$-cycloalkyl, $C_5$-$C_6$-cycloalkenyl, $C_5$-$C_{14}$-cycloalkylcycloalkyl or $S(O)_m$ $R^b$, wherein the C-atoms of the aforementioned groups may be unsubstituted, or partially or fully substituted by $R^{2a}$.

In an embodiment, $R^2$ is hydrogen, halogen, CN, $C_1$-$C_6$-alkyl, $C_1$-$C_2$-alkoxy-$C_1$-$C_2$-alkyl or $C_3$-$C_6$-cycloalkyl, wherein the C-atoms of the aforementioned groups may be substituted by halogen or CN.

In an embodiment, $R^2$ is hydrogen, halogen, CN or $C_1$-$C_4$-alkyl which may be substituted by halogen.

In a further embodiment $R^2$ is ON.

In a further embodiment, $R^2$ is hydrogen or $C_1$-$C_2$-alkyl, particularly $CH_3$.

In a further embodiment, $R^2$ is $C_1$-$C_6$-haloalkyl, preferably $C_1$-$C_2$-haloalkyl, particularly halomethyl, such as $CF_3$ or $CHF_2$.

In another embodiment, $R^2$ is $C_1$-$C_2$-alkoxy-$C_1$-$C_2$-alkyl, preferably $C_1$-$C_2$-alkoxy-methyl, particularly $CH_2OCH_3$.

In another embodiment, $R^2$ is $C_3$-$C_6$-cycloalkyl, preferably cyclopropyl which may be substituted, preferably by halogen or cyano.

In another embodiment, $R^2$ is $C_2$-$C_6$-alkyl, preferably $C_2$-$C_4$-alkyl, particularly $CH_2CH_3$ or $C(CH_3)_3$.

In another embodiment, $R^2$ is $C_1$-$C_6$-alkyl, preferably $C_1$-$C_2$-alkyl, particularly $CH_3$.

In another embodiment, $R^2$ is halogen, preferably Cl or F, particularly F.

In another embodiment, $R^2$ is a five- or six-membered carbo- or heterocyclic ring, which ring may be unsubstituted, partially, or fully substituted by $R^{2a}$, and wherein $R^{2a}$ is as hereunder defined or $R^{2a}$ is preferably halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by halogen, $C_1$-$C_6$-haloalkyl or $C_1$-$C_6$-haloalkoxy.

In a further embodiment, $R^2$ is a six-membered carbo- or heterocyclic ring, which ring may be unsubstituted, partially, or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by $R^{2aa}$, wherein $R^{2aa}$ is as hereunder defined.

In a further embodiment, $R^2$ is a six-membered aromatic carbocyclic ring, which ring may be unsubstituted, partially, or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl which may be substituted by $R^{2aa}$, wherein $R^{2aa}$ is as hereunder defined, preferably $R^{2aa}$ is halogen, $C_1$-$C_6$-haloalkyl or $C_1$-$C_6$-haloalkoxy.

Within this embodiment, $R^2$ is phenyl which may be substituted by halogen, $C_1$-$C_6$-haloalkyl or $C_1$-$C_6$-haloalkoxy.

In a further embodiment, $R^2$ is a six-membered heterocyclic ring, which contains 1 or 2, preferably 1, heteroatom(s) selected from N—$R^c$, O, and S, wherein S may be oxidised, which heterocyclic ring is unsubstituted or substituted by one or more groups $R^{2a}$, wherein $R^{2a}$ is as hereunder defined.

In an embodiment, $R^a$ is halogen, $C_1$-$C_6$-haloalkyl, $C_1$-$C_6$-alkoxy, $C_1$-$C_6$-haloalkoxy, $OR^c$, $C(=O)OR^c$, $C(=O)NR^bR^c$, or phenyl, wherein the C-atoms of the aforementioned groups may be unsubstituted or substituted by one or more $R^{1aa}$, wherein $R^{1aa}$ is as hereunder defined; particularly $R^a$ is halogen, $C_1$-$C_6$-alkoxy, or $C_1$-$C_6$-haloalkoxy. In an embodiment, $R^a$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms aforementioned which groups may be unsubstituted or substituted by one or more $R^{1aa}$, wherein $R^{1aa}$ is as hereunder defined.

In a further embodiment, $R^a$ is halogen, $C_1$-$C_4$-alkyl, $C_1$-$C_4$-haloalkyl or $C_3$-$C_6$-cycloalkyl.

In another embodiment, $R^a$ is halogen, $C_1$-$C_4$-haloalkyl, $C_1$-$C_6$-alkoxy or $C_1$-$C_6$-haloalkoxy.

In a further embodiment, $R^a$ is halogen, $C_1$-$C_4$-haloalkyl or $C_1$-$C_6$-alkoxy.

In another embodiment, $R^a$ is halogen, $C_1$-$C_4$-haloalkyl or $C_1$-$C_6$-haloalkoxy.

In a another embodiment, $R^a$ is phenyl which may be substituted by one or more $R^{1aa}$.

In another embodiment, $R^a$ is $C_1$-$C_6$-haloalkyl, preferably $C_1$-$C_2$-haloalkyl, e.g. halomethyl such as $CHF_2$ or $CF_3$, particularly $CF_3$.

In another embodiment, $R^a$ is $C_1$-$C_6$-haloalkoxy.

In an embodiment, $R^a$ is halogen, CN, $NO_2$, $S(O)_mR^b$, $C(O)R^c$, $C(O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted by $R^{1aa}$, wherein $R^{1aa}$ is as hereunder defined.

In a further embodiment, $R^a$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted by $R^{aa}$, wherein $R^{aa}$ is as hereunder defined.

In a further embodiment, $R^a$ is, $C(=O)OR^c$ or $C(=O)NR^bR^c$.

In a further embodiment, $R^a$ is halogen, CN or $C_1$-$C_2$-haloalkyl.

In a further embodiment, $R^a$ is halogen or $C_1$-$C_2$-haloalkyl.

In a further embodiment, $R^a$ is halogen or $C_1$-$C_2$-haloalkoxy.

In an embodiment, $R^a$ is halogen, preferably Br, Cl or F, particularly Cl.

In an embodiment, two geminally bound groups $R^a$ together may form a group selected from =O, =S, =$CR^bR^c$, =$NR^c$, =$NOR^c$, and =$NNR^cR^c$;

In another embodiment, two geminally bound groups $R^a$ together may form a group selected from =$CR^bR^c$, =$NR^c$, =$NOR^c$, and =$NNR^cR^c$;

In another embodiment, two geminally bound groups $R^a$ together may form a group selected from =O, =S and =$N(C_1$-$C_6$-alkyl).

In another embodiment, two geminally bound groups $R^a$ together may form a =$N(C_1$-$C_6$-alkyl) group.

In an embodiment, $R^b$ is hydrogen, $C_1$-$C_6$-alkyl, $C_1$-$C_6$-haloalkyl, $C_1$-$C_6$-alkoxy, $C_1$-$C_6$-haloalkoxy, phenyl, pyridyl, thiazyl or thienyl, wherein the C-atoms of the aforementioned groups may be substituted by $R^{aa}$, wherein $R^{aa}$ is as hereunder defined. In a further embodiment, $R^b$ is hydrogen, $C_1$-$C_6$-alkyl, $C_1$-$C_6$-haloalkyl, $C_1$-$C_6$-alkoxy or $C_1$-$C_6$-haloalkoxy. In a further embodiment, $R^b$ is hydrogen, $C_1$-$C_6$-alkyl or $C_1$-$C_6$-haloalkyl. In an embodiment, $R^b$ is $C_1$-$C_6$-alkyl or $C_1$-$C_6$-haloalkyl. In an embodiment, $R^b$ is H.

In an embodiment, $R^c$ is hydrogen, $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the C-atoms of the aforementioned groups may be substituted by $R^{aa}$, wherein $R^{aa}$ is as hereunder defined. In a further embodiment, $R^c$ is hydrogen, $C_1$-$C_4$-alkyl, $C_1$-$C_4$-haloalkyl, $C_1$-$C_4$-alkylcarbonyl, or $C_1$-$C_6$-cycloalkyl. In an embodiment, $R^c$ is hydrogen, $C_1$-$C_6$-alkyl or $C_1$-$C_6$-haloalkyl. In an embodiment, $R^c$ is $C_1$-$C_6$-alkyl or $C_1$-$C_6$-haloalkyl. In an embodiment, $R^c$ is H.

In an embodiment, two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted by $R^3$.

In another embodiment, two geminally bound groups $R^bR^b$, $R^cR^b$ or $R^cR^c$ together with the atom to which they are bound, may form a 5- or 6-membered saturated, partially unsaturated or aromatic carbocyclic ring, which ring may be partially or fully substituted by $R^3$, and wherein $R^3$ is as hereunder defined.

In another embodiment, two geminally bound groups $R^bR^b$, $R^cR^b$ or $R^cR^c$ together with the atom to which they are bound, may form a 5- or 6-membered saturated, partially unsaturated or aromatic heterocyclic ring, which may contain 1 to 2 heteroatoms or heteroatoms groups selected from N, O, S, NO, SO and $SO_2$, wherein the heterocyclic ring may be partially or fully substituted by $R^3$, and wherein $R^3$ is as hereunder defined.

In an embodiment, $R^d$ is hydrogen, phenyl, $C_1$-$C_4$-alkyl or $C_2$-$C_6$-alkenyl, wherein the aforementioned groups may be substituted by one or more halogen. In a further embodiment, $R^d$ is $C_1$-$C_4$-alkyl or phenyl, which may be substituted by halogen. In another embodiment, $R^c$ $C_1$-$C_4$-alkyl, preferably $CH_3$.

In an embodiment, $R^e$ is $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the aforementioned groups may be substituted by $R^{aa}$, wherein $R^{aa}$ is as hereunder defined. In a further embodiment, $R^e$ is $C_1$-$C_4$-alkyl, $C_1$-$C_4$-haloalkyl, $C_1$-$C_4$-alkylcarbonyl, or $C_1$-$C_6$-cycloalkyl. In a further embodiment, $R^e$ is $C_1$-$C_4$-alkyl or $C_1$-$C_4$-haloalkyl.

In an embodiment, $R^{aa}$ is halogen, $C_1$-$C_6$-alkyl or $C_1$-$C_6$-haloalkyl. In another embodiment, $R^{aa}$ is $C_1$-$C_6$-alkoxy or $C_1$-$C_6$-haloalkoxy. In an embodiment, $R^{aa}$ is halogen.

In an embodiment, $R^{2a}$ is halogen, $C_1$-$C_6$-haloalkyl, $C_1$-$C_6$-alkoxy, $C_1$-$C_6$-haloalkoxy, $OR^c$, $C(=O)OR^c$, $C(=O)NR^bR^c$, or phenyl, wherein the C-atoms of the aforementioned groups may be unsubstituted or substituted by one or more $R^{2aa}$, wherein $R^{2aa}$ is as hereunder defined, particularly $R^{2a}$ is halogen, $C_1$-$C_6$-alkoxy, or $C_1$-$C_6$-haloalkoxy.

In an embodiment, two geminally bound groups $R^{2a}$ together may form a group selected from =O, =S and =N($C_1$-$C_6$-alkyl).

In an embodiment, $R^{2a}$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms of the aforementioned groups may be unsubstituted or substituted by one or more $R^{2aa}$, wherein $R^{2aa}$ is as hereunder defined.

In a further embodiment, $R^{2a}$ is halogen, $C_1$-$C_4$-haloalkyl or $C_3$-$C_6$-haloalkoxy.

In a another embodiment, $R^{2a}$ is phenyl which may be substituted by one or more $R^{2aa}$.

In a another embodiment, $R^{2a}$ is halogen. In another embodiment, $R^{2a}$ is $C_1$-$C_6$-haloalkyl. In another embodiment, $R^{2a}$ is $C_1$-$C_6$-haloalkoxy.

In another embodiment, $R^{2a}$ is halogen, CN, $NO_2$, $S(O)_m R^b$, $C(=O)R^c$, $C(=O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted by $R^{aa}$, wherein is as hereunder defined.

In further embodiment, $R^{2a}$ is, $C(=O)OR^c$ or $C(=O)NR^bR^c$.

In another embodiment, $R^{2a}$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted by $R^{2aa}$, wherein $R^{2aa}$ is as hereunder defined.

In an embodiment, $R^{2a}$ is Br, Cl or F, particularly Cl.

In another embodiment, $R^{2a}$ is $C_1$-$C_2$-haloalkyl, preferably halomethyl such as $CHF_2$ or $CF_3$, particularly $CF_3$.

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), $C(=O)N(C_1$-$C_6$-alkyl)($C_1$-$C_6$-alkyl), $S(O)_m$($C_1$-$C_6$-alkyl), $SO_2N(C_1$-$C_6$-alkyl)($C_1$-$C_6$-alkyl), $OSO_2(C_1$-$C_6$-alkyl), $N(C_1$-$C_6$-alkyl)$SO_2(C_1$-$C_6$-alkyl), or $S(=O)_p(=N(C_1$-$C_6$-alkyl))($C_1$-$C_6$-alkyl) or two geminally bound groups $R^{2aa}$ together may form a group selected from =O, =S and =N($C_1$-$C_6$-alkyl).

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), $C(=O)N(C_1$-$C_6$-alkyl)($C_1$-$C_6$-alkyl), $S(O)_m$($C_1$-$C_6$-alkyl), $SO_2N(C_1$-$C_6$-alkyl)($C_1$-$C_6$-alkyl), $OSO_2(C_1$-$C_6$-alkyl), $N(C_1$-$C_6$-alkyl)$SO_2(C_1$-$C_6$-alkyl), or $S(=O)_p(=N(C_1$-$C_6$-alkyl))($C_1$-$C_6$-alkyl). In another embodiment, two geminally bound groups $R^{2aa}$ together may form a group selected from =O, =S and =N($C_1$-$C_6$-alkyl).

In an embodiment, $R^3$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), $C(=O)N(C_1$-$C_6$-alkyl)($C_1$-$C_6$-alkyl), $S(O)_m$($C_1$-$C_6$-alkyl), $SO_2N(C_1$-$C_6$-alkyl)($C_1$-$C_6$-alkyl), $OSO_2(C_1$-$C_6$-alkyl), $N(C_1$-$C_6$-alkyl)$SO_2(C_1$-$C_6$-alkyl), $S(=O)_p(=N(C_1$-$C_6$-alkyl))($C_1$-$C_6$-alkyl), or two geminally bound groups $R^3$ together may form a group selected from =O, =S and =N($C_1$-$C_6$-alkyl).

In an embodiment, $R^3$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), $C(=O)N(C_1$-$C_6$-alkyl)($C_1$-$C_6$-alkyl), $S(O)_m$($C_1$-$C_6$-alkyl), $SO_2N(C_1$-$C_6$-alkyl)($C_1$-$C_6$-alkyl), $OSO_2(C_1$-$C_6$-alkyl), $N(C_1$-$C_6$-alkyl)$SO_2(C_1$-$C_6$-alkyl), or $S(=O)_p(=N(C_1$-$C_6$-alkyl))($C_1$-$C_6$-alkyl). In another embodiment, two geminally bound groups $R^3$ together may form a group selected from =O, =S and =N($C_1$-$C_6$-alkyl).

In an embodiment, m is 0. In another embodiment, m is 1. In another embodiment, m is 2.

In an embodiment, n is 0. In another embodiment, n is 1. In another embodiment, n is 2.

In an embodiment, p is 0. In another embodiment, p is 1.

In particular, with a view to their use, preference is given to the compounds of the formula (I) compiled in the tables below, which compounds correspond to the compounds of formulae I.1.B (i.e. wherein X and Y are O) and to the preferred compounds of formula II-1, II-2, and II-3. Each of the groups mentioned for the substituents in the tables are furthermore per se, independently of the combination in which they are mentioned, a particularly preferred aspect of the substituent in question. Further, each individual meaning of a substituent in the tables constitutes a particularly preferred embodiment of the substituents in question.

Table 1: Compounds of the formula (III-1) corresponding to the compounds of the formula II-1, in which X and Y are O, and the combination of $R^1$, $ZR^2$ for a compound corresponds in each case to one line of Table A:

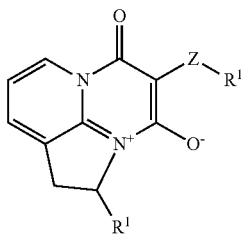
(III-1)

Table 2: Compounds of the formula (III-2) corresponding to the compounds of the formula II-2, in which X and Y are O, and the combination of $R^1$, $ZR^2$ for a compound corresponds in each case to one line of Table A:

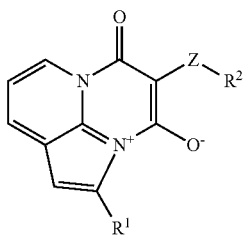
(III-2)

Table 3: Compounds of the formula (III-3) corresponding to the compounds of the formula II-3, in which X and Y are O, and the combination of $R^1$, $ZR^2$ for a compound corresponds in each case to one line of Table A.

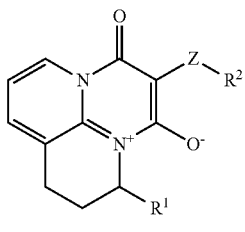
(III-3)

Table 4: Compounds of the formula (III-4) corresponding to the compounds of the formula II-7, in which X and Y are O, and the combination of $R^1$, $ZR^2$ for a compound corresponds in each case to one line of Table A.

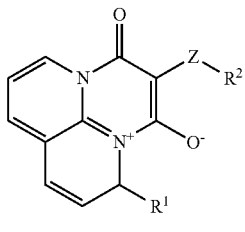
(III-7)

TABLE A

| No. | $ZR^2$ | $R^1$ |
|---|---|---|
| A-1 | $C_6H_5$ | D-9b |
| A-2 | 2-F-C₆H₄ | D-9b |
| A-3 | 2-OCH₃-C₆H₄ | D-9b |
| A-4 | 2,4-F₂-C₆H₃ | D-9b |
| A-5 | 2,6-F₂-C₆H₃ | D-9b |
| A-6 | 4-F-C₆H₄ | D-9b |
| A-7 | $CO_2CH_2CH_3$ | D-9b |
| A-8 | $C(O)CF_3$ | D-9b |
| A-9 | $C(O)C_6H_5$ | D-9b |
| A-10 | 3-OCH₃-C₆H₄ | D-9b |
| A-11 | 3-CN-C₆H₄ | D-9b |
| A-12 | $3\text{-}(CO_2CH_2CH_3)C_6H_5$ | D-9b |
| A-13 | $3\text{-}(C(O)N(CH_3)_2)C_6H_5$ | D-9b |
| A-14 | 3-CF₃-C₆H₄ | D-9b |
| A-15 | 3-OCF₃-C₆H₄ | D-9b |

TABLE A-continued

| No. | ZR² | R¹ |
|---|---|---|
| A-16 | 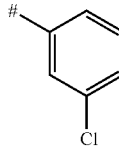 3,5-dichlorophenyl | D-9b |
| A-17 | 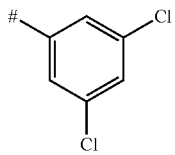 3,5-dichlorophenyl | D-9b |
| A-18 | 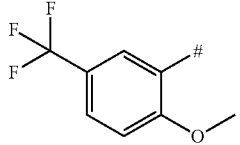 4-methoxy-2-trifluoromethylphenyl (attached at #) | D-9b |
| A-19 | 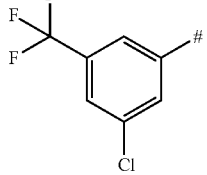 3-chloro-5-trifluoromethylphenyl | D-9b |
| A-20 | 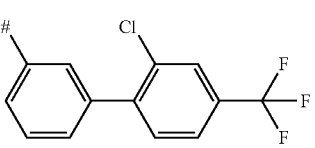 2'-chloro-4'-trifluoromethylbiphenyl-3-yl | D-9b |
| A-21 | 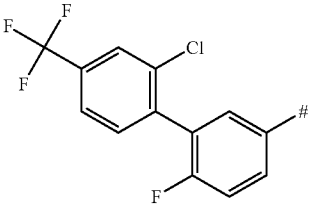 | D-9b |
| A-22 | 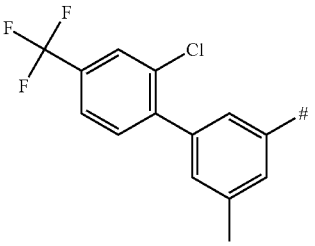 | D-9b |
| A-23 | C₆H₅ | D-2b |
| A-24 | 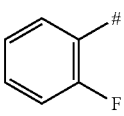 2-fluorophenyl | D-2b |
| A-25 | 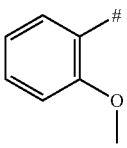 2-methoxyphenyl | D-2b |
| A-26 | 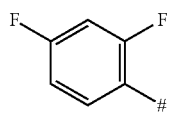 2,5-difluorophenyl | D-2b |
| A-27 | 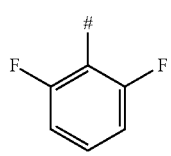 2,6-difluorophenyl | D-2b |
| A-28 | 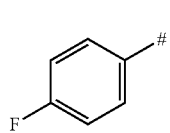 4-fluorophenyl | D-2b |
| A-29 | CO₂CH₂CH₃ | D-2b |
| A-30 | C(O)CF₃ | D-2b |
| A-31 | C(O)C₆H₅ | D-2b |
| A-32 | 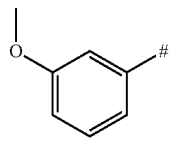 3-methoxyphenyl | D-2b |
| A-33 | 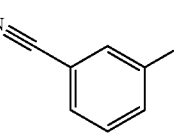 3-cyanophenyl | D-2b |
| A-34 | 3-(CO₂CH₂CH₃)C₆H₅ | D-2b |
| A-35 | 3-(C(O)N(CH₃)₂)C₆H₅ | D-2b |
| A-36 | 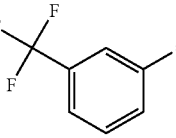 3-trifluoromethylphenyl | D-2b |
| A-37 | 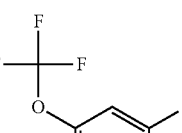 3-trifluoromethoxyphenyl | D-2b |
| A-38 | 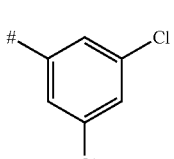 3,5-dichlorophenyl | D-2b |

TABLE A-continued

| No. | ZR² | R¹ |
|---|---|---|
| A-39 | 3-methyl-5-fluorophenyl (# at 1) | D-2b |
| A-40 | 2-methoxy-5-(trifluoromethyl)phenyl (# at position) | D-2b |
| A-41 | 3-chloro-5-(trifluoromethyl)phenyl | D-2b |
| A-42 | 2-chloro-4-(trifluoromethyl)biphenyl-3'-yl | D-2b |
| A-43 | 2'-fluoro-2-chloro-4-(trifluoromethyl)biphenyl-3'-yl... | D-2b |
| A-44 | 5'-methyl-2-chloro-4-(trifluoromethyl)biphenyl-3'-yl | D-2b |
| A-45 | C₆H₅ | D-25a |
| A-46 | 2-fluorophenyl | D-25a |
| A-47 | 2-methoxyphenyl | D-25a |
| A-48 | 2,6-difluorophenyl | D-25a |
| A-49 | 2,6-difluorophenyl | D-25a |
| A-50 | 4-fluorophenyl | D-25a |
| A-51 | CO₂CH₂CH₃ | D-25a |
| A-52 | C(O)CF₃ | D-25a |
| A-53 | C(O)C₆H₅ | D-25a |
| A-54 | 3-methoxyphenyl | D-25a |
| A-55 | 3-cyanophenyl | D-25a |
| A-56 | 3-(CO₂CH₂CH₃)C₆H₅ | D-25a |
| A-57 | 3-(C(O)N(CH₃)₂)C₆H₅ | D-25a |
| A-58 | 3-(trifluoromethyl)phenyl | D-25a |
| A-59 | 3-(trifluoromethoxy)phenyl | D-25a |
| A-60 | 3,5-dichlorophenyl | D-25a |
| A-61 | 3-methyl-5-fluorophenyl | D-25a |
| A-62 | 4-methoxy-2-(trifluoromethyl)phenyl | D-25a |

TABLE A-continued

| No. | ZR² | R¹ |
|---|---|---|
| A-63 | 3-chloro-5-(trifluoromethyl)phenyl (# attachment) | D-25a |
| A-64 | 2'-chloro-4'-(trifluoromethyl)biphenyl-3-yl (# attachment) | D-25a |
| A-65 | 2'-chloro-4'-(trifluoromethyl)-2-fluoro-biphenyl-3-yl (# attachment) | D-25a |
| A-66 | 2'-chloro-4'-(trifluoromethyl)-5-methyl-biphenyl-3-yl (# attachment) | D-25a |

The compound of formula (I) according to the present invention can be prepared according to the following syntheses routes, e.g. according to the preparation methods and preparation schemes as described below.

The compound of formula (I) according to the present invention can be prepared according to the e.g. preparation methods and preparation schemes as described below.

The compounds used as starting materials for the syntheses of the compounds according to the present invention can generally be prepared by standard methods of organic chemistry. If not otherwise specified, the definitions of the variables such as X, Y, R¹ and R² of the structures given in the schemes have the same meaning as defined above.

Mesoionic heterocycles analogous to compounds of formula (I) have been described in Stadlbauer, W.; Ravao, Y.; Sterk, H. and Kappe, T.; Monatshefte für Chemie, 114, 965-972; 1983. Compounds of formula (I) can be prepared analogous to the methods described by Holyoke et al. in WO 2009/099929 (Scheme 1), from appropriately substituted compounds P-1.

Scheme 1

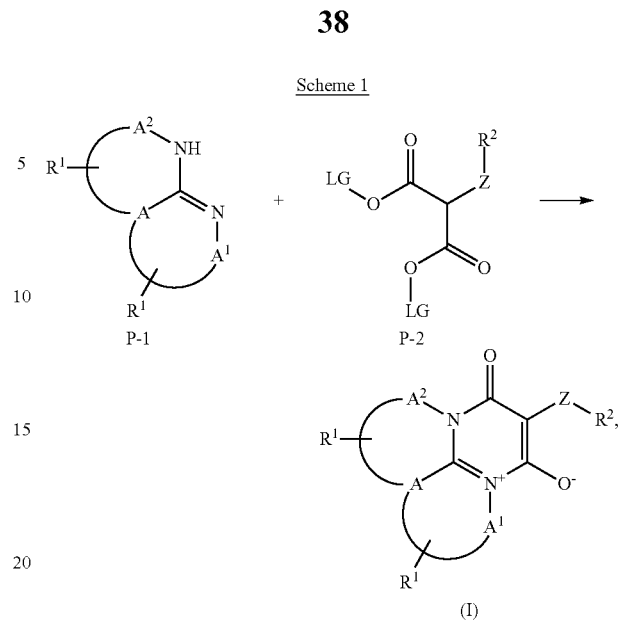

wherein LG is a leaving group and the remaining substituents are as herein defined.

Heterocycles like P-1 are widespread in the chemical literature. Methods of their preparation can be found e. g. in Science of Synthesis, Georg Thieme Verlag Stuttgart. As an example, 2,3-dihydro-1H-pyrrolo[2,3-b]pyridines like P-5 can be synthesized by reduction of the corresponding 1H-pyrrolo[2,3-b]pyridines P-4 (Scheme 2). Reducing agents can be for example, but not exclusively, hydrogen together with a metal catalyst like nickel, palladium platinum or copper (see e.g. Clemo, G. R. and Swan, G. A.; Journal of the Chemical Society, 603-7; 1945), or borohydride reagents, for example sodium borohydride or borane.

Scheme 2

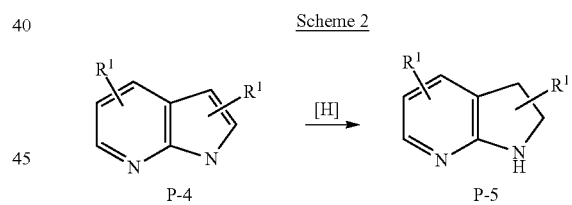

2 Substituted 1H-pyrrolo[2,3-b]pyridines P-4 are for example available by cyclisation from 3-alkinyl aminopyridines like P-6, which in turn can be obtained by Sonogashira coupling (see Chinchilla, Rafael; Najera, Carmen, Chemical Society Reviews (2011), 40(10), 5084-5121.)(Scheme 3). For the cyclisation reaction see e.g. Carlos de Mattos, Marcos et al, Synthesis, (14), 2149-2152; 2007.

Scheme 3

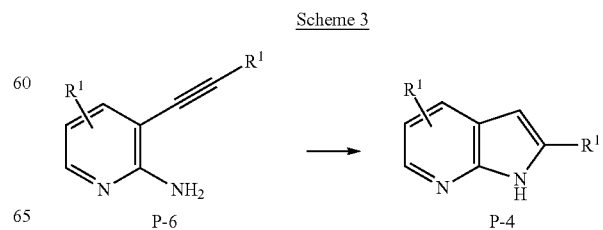

Compounds like P-4 can also be made e.g. via palladium coupling of an appropriately substituted amino pyridine like P-7 and a methyl ketone like P-8 (Scheme 4). This has been described in Spergel, Steven H. et al, Journal of Organic Chemistry, 75(15), 5316-5319; 2010.

Scheme 4

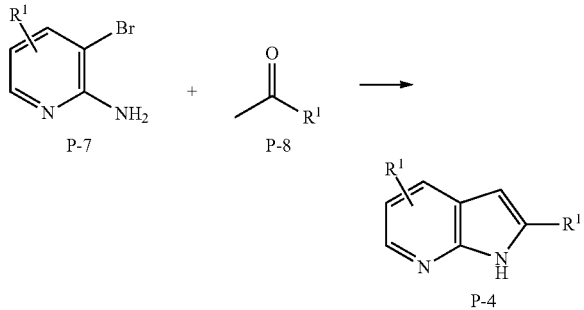

As an additional example 2-substituted-1,2,3,4-tetrahydro-1,8-naphthyridines like P-10 are available from the corresponding 1H-1,8-naphthyridin-4-ones P-9 (scheme 5) as described in Carboni, S. et al, Farmaco, Edizione Scientifica, 33(5), 315-23; 1978.

Scheme 5

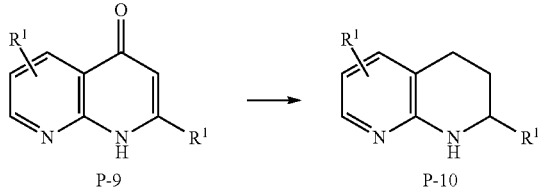

1H-1,8-naphthyridin-4-ones (P-9) can be made by various methods found e.g. in D'Andrea, Stanley and Scola, Paul Michael, U.S. Pat. Appl. Publ., 20080107623, 08 May 2008.

If individual compounds cannot be prepared via the above described routes, they can be prepared by derivatization of other compounds of formula (I) or by customary modifications of the synthesis routes described.

For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or silica gel.

The term "invertebrate pest" as used herein encompasses animal populations, such as arthropod pests, including insects and arachnids, as well as nematodes, which may attack plants thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The compounds of formula (I) according to the present invention are in particular suitable for efficiently controlling arthropod pests such as arachnids, myriapedes and insects as well as nematodes.

The compounds of the formula (I) are especially suitable for efficiently combating the following pests:

Insects from the order of the lepidopterans (Lepidoptera), for example *Agrotis ipsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Tuta absoluta* and *Zeiraphera canadensis;* beetles (Coleoptera), for example *Agrilus sinuatus, Agriotes lineatus, Agriotes obscurus, Amphimallus solstitialis, Anisandrus dispar, Anoplophora glabripennis, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctata, Diabrotica 12-punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga sp., Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophi-*

*lus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza florum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola, Tabanus similis, Tipula oleracea*, and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis*, and *Coptotermes formosanus;* cockroaches (Blattaria-Blattodea), e.g. *Blattella germanica, Blattella asahinae, Periplaneta americana, Periplaneta japonica, Periplaneta brunnea, Periplaneta fuligginosa, Periplaneta australasiae*, and *Blatta orientalis;* bugs, aphids, leafhoppers, whiteflies, scale insects, cicadas, Pentatomidae (Hemiptera), e.g. *Acrosternum* spp.; like *Acrosternum hilare, Blissus leucopterus, Cyrtopeltis notatus, Dectes texanus, Dysdercus cingulatus, Dysdercus intermedius, Eurygaster integriceps, Euschistus* spp.; like *Euschistos heros, Euschistus impictiventris, Euschistus servus, Halyomorpha halys, Leptoglossus phyllopus, Lygus lineolaris, Lygus pratensis, Megacopta cribraria, Nezara* spp., like *Nezara viridula, Piesma quadrata, Solubea insularis, Piezodorus* spp. like *Piezodorus guildinii, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus*, and *Linepithema humile;* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera*, and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei*, and *Eriophyidae* spp. such as *Aculus schlechtendali, Phyllocoptrata oleivora* and *Eriophyes sheldoni; Tarsonemidae* spp. such as *Phytonemus pallidus* and *Polyphagotarsonemus latus; Tenuipalpidae* spp. such as *Brevipalpus phoenicis; Tetranychidae* spp. such as *Tetranychus cinnabarinus, Tetranychus kanzawai, Tetranychus pacificus, Tetranychus telarius* and *Tetranychus urticae, Panonychus ulmi, Panonychus citri*, and *Oligonychus pratensis; Araneida*, e.g. *Latrodectus mactans*, and *Loxosceles reclusa;* fleas (Siphonaptera), e.g. *Ctenocephalides felis, Ctenocephalides canis, Xenopsylla cheopis, Pulex irritans, Tunga penetrans*, and *Nosopsyllus fasciatus*, silverfish, firebrat (Thysanura), e.g. *Lepisma saccharina* and *Thermobia domestica*, centipedes (Chilopoda), e.g. *Scutigera coleoptrata*, millipedes (Diplopoda), e.g. *Narceus* spp., Earwigs (Dermaptera), e.g. *forficula auricularia*, lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

The compounds of formula (I) are also suitable for controlling Nematodes: plant parasitic nematodes such as root knot nematodes, *Meloidogyne hapla, Meloidogyne incognita, Meloidogyne javanica*, and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodo-*

*rus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula (I) are particularly useful for controlling, or combating, or treating, or preventing or protecting each of the individual group of target pests as above listed as well as each combination thereof.

Each of the groups or subgroup of the above listed pests constitute per se, independently of every possible combination a particular preferred target pests for which the compounds of the present invention are useful and therefore particular embodiment. Useful in this context is to be understood as:

use for combating such pest(s) or,
use for controlling such pest(s) or,
use for protecting from attack by such pest(s) or,
use for treating against infestation or infection by such pest(s) or,
use for controlling against infestation or infection by such pest(s) or,
use for preventing against infestation or infection by such pest(s) or,
use for protecting against infestation or infection by such pest(s).

The compounds of the formula (I) are particularly useful for controlling insects, preferably piercing-sucking insects such as insects from the genera Thysanoptera, Diptera and Hemiptera.

Compounds of the formula (I) are particularly useful for controlling insects of the orders Hemiptera and Thysanoptera.

For use in a method according to the present invention, the compounds of formula (I) can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of formula (I) according to the invention.

An agrochemical composition according to the present invention comprises a pesticidally effective amount of a compound of formula (I) according to the present invention. The term "effective amount" denotes an amount of the composition or of the compounds of formula (I), which is sufficient for controlling animal pests on a locus, such as crops, cultivated plants or in the protection of materials and which does not result in a substantial damage to the treated plants. Such an amount can vary in a broad range and is dependent on various factors, such as the animal pest species to be controlled, the treated cultivated plant or material, the climatic conditions and the specific compound of formula (I) used.

The compounds of formula (I) according to the invention can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries for the formulations and or the agrochemicals compositions according to the inventions are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, antifreezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclo-hexanol; glycols; DMSO; ketones, e.g. cyclohexanone; esters, e.g. lactates, carbonates, fatty acid esters, gammabutyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, lime-stone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long chain primary amines. Suitable amphoteric surfactants are alkylbetains and imidazolines. Suitable block polymers are block polymers of the A-B or A-B-A type comprising blocks of polyethylene oxide and poly-propylene oxide, or of the A-B-C type comprising alkanol, polyethylene oxide and polypropyl-ene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound of formula (I) on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable antifreezing agents are ethylene glycol, propylene glycol, urea and glycerine.

Suitable antifoaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water soluble concentrates (SL, LS)
   10-60 wt % of a compound of formula (I) according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.
ii) Dispersible concentrates (DC)
   5-25 wt % of a compound of formula (I) according to the invention and 1-10 wt % dispersant (e. g. polyvinylpyrrolidone) are dissolved in up to 100 wt % organic solvent (e.g. cyclohexanone). Dilution with water gives a dispersion.
iii) Emulsifiable concentrates (EC)
   15-70 wt % of a compound of formula (I) according to the invention and 5-10 wt % emulsifiers (e.g. calcium dodecylbenzenesulfonate and castor oil ethoxylate) are dissolved in up to 100 wt % water insoluble organic solvent (e.g. aromatic hydrocarbon). Dilution with water gives an emulsion.
iv) Emulsions (EW, EO, ES)
   5-40 wt % of a compound of formula (I) according to the invention and 1-10 wt % emulsifiers (e.g. calcium dodecylbenzenesulfonate and castor oil ethoxylate) are dissolved in 20-40 wt % water insoluble organic solvent (e.g. aromatic hydrocarbon). This mixture is introduced into up to 100 wt % water by means of an emulsifying machine and made into a homogeneous emulsion. Dilution with water gives an emulsion.
v) Suspensions (SC, OD, FS)
   In an agitated ball mill, 20-60 wt % of a compound of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.
vi) Water dispersible granules and water soluble granules (WG, SG)
   50-80 wt % of a compound of formula (I) according to the invention are ground finely with addition of up to 100 wt % dispersants and wetting agents (e.g. sodium lignosulfonate and alcohol ethoxylate) and prepared as water dispersible or water soluble granules by means of technical appliances (e. g. extrusion, spray tower, fluidized bed). Dilution with water gives a stable dispersion or solution of the active substance.
vii) Water dispersible powders and water-soluble powders (WP, SP, WS)
   50-80 wt % of a compound of formula (I) according to the invention are ground in a rotor stator mill with addition of 1-5 wt % dispersants (e.g. sodium lignosufonate), 1-3 wt % wetting agents (e.g. alcohol ethoxylate) and up to 100 wt % solid carrier, e.g. silica gel. Dilution with water gives a stable dispersion or solution of the active substance.
viii) Gel (GW, GF)
   In an agitated ball mill, 5-25 wt % of a compound of formula (I) according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.
iv) Microemulsion (ME)
   5-20 wt % of a compound of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

iv) Microcapsules (CS)

An oil phase comprising 5-50 wt % of a compound of formula (I) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth) acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.

ix) Dunstable powders (DP, DS)

1-10 wt % of a compound of formula (I) according to the invention are ground finely and mixed intimately with up to 100 wt % solid carrier, e.g. finely divided kaolin.

x) Granules (GR, FG)

0.5-30 wt % of a compound of formula (I) according to the invention is ground finely and associated with up to 100 wt % solid carrier (e.g. silicate). Granulation is achieved by extrusion, spray drying or the fluidized bed.

xi) Ultra-low volume liquids (UL)

1-50 wt % of a compound of formula (I) according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % antifreezing agents, 0.1-1 wt % antifoaming agents, and 0.1-1 wt % colorants.

The agrochemical compositions generally comprise between 0.01 and 95%, preferably between 0.1 and 90%, and most preferably between 0.5 and 75%, by weight of active substance i.e. the compounds of formula (I) according to the invention. The active substances are generally employed in a purity of from 90% to 100%, preferably from 95% to 100% (according to NMR spectrum).

Water soluble concentrates (LS), Suspoemulsions (SE), flowable concentrates (FS), powders for dry treatment (DS), water dispersible powders for slurry treatment (WS), water soluble powders (SS), emulsions (ES), emulsifiable concentrates (EC) and gels (GF) are usually employed for the purposes of treatment of plant propagation materials, particularly seeds.

The compositions according to the invention in question give, after two-to-tenfold dilution, concentrations of active substance of from 0.01 to 60% by weight, preferably from 0.1 to 40% by weight, in the ready-to-use preparations.

Application can be carried out before or during sowing. Methods for applying or treating compound of formula (I) and compositions thereof, respectively, on to plant propagation material, especially seeds include dressing, coating, pelleting, dusting, soaking and in furrow application methods of the propagation material. Preferably, compound of formula (I) or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilo-gram of plant propagation material (preferably seed) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment of the present invention, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of formula (I) and/or additional active substances from the groups M.1) to M.26, including M-X or F.I to F.XII, may be mixed by the user in a spray tank and further auxiliaries and additives may be added, if appropriate.

In a further embodiment, either individual components of the composition according to the invention or partially premixed components, e. g. components comprising compounds of formula (I) and/or active substances from the groups M.1 to M.26, including M-X or F.I to F.XII, can be applied jointly (e.g. after tank mix) or consecutively.

The following list M of pesticides, grouped and numbered according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifosmethyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, del-tamethrin, empenthrin, esfenvalerate, etofenprox, fenpropathrin, fenvalerate, flucythrinate, flumethrin, tau-fluvalinate, halfenprox, hep tafluthrin, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstakiand bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b) N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e) N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;

M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide;

M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide;

M.28.5k) 3-Bromo-N-[2,4-dichloro-6-(methylcarbamoyl)phenyl]-1-(3,5-dichloro-2-pyridyl)-1H-pyrazole-5-carboxamide;

M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide;

or a compound selected from

M.28.6: N-(2-cyanopropan-2-yl)-N-(2,4-dimethylphenyl)-3-iodobenzene-1,2-dicarboxamide; or M.28.7: 3-Chloro-N-(2-cyanopropan-2-yl)-N-(2,4-dimethylphenyl)-benzene-1,2-dicarboxamide;

M.28.8a) 1-(3-Chloro-2-pyridinyl)-N-[4-cyano-2-methyl-6-[(methylamino)carbonyl]phenyl]-3-[[5-(trifluoromethyl)-2H-tetrazol-2-yl]methyl]-1H-pyrazole-5-carboxamide; or M.28.8b) 1-(3-Chloro-2-pyridinyl)-N-[4-cyano-2-methyl-6-[(methylamino)carbonyl]phenyl]-3-[[5-(trifluoromethyl)-1H-tetrazol-1-yl]methyl]-1H-pyrazole-5-carboxamide;

M.UN. insecticidal active compounds of unknown or uncertain mode of action, as for example afidopyropen, afoxolaner, azadirachtin, amidoflumet, benzoximate, bifenazate, bromo-propylate, chinomethionat, cryolite, dicofol, flufenerim, flometoquin, fluensulfone, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.UN.3: 11-(4-chloro-2,6-dimethylphenyl)-12-hydroxy-1,4-dioxa-9-azadispiro[4.2.4.2]-tetradec-11-en-10-one, or the compound M.UN.4: 3-(4'-fluoro-2,4-dimethylbiphenyl-3-yl)-4-hydroxy-8-oxa-1-azaspiro[4.5]dec-3-en-2-one, or the compound M.UN.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, I-1582); or a compound selected from the group of M.UN.6, wherein the compound is selected from M.UN.6a) to M.UN.6k):

M.UN.6a) (E/Z)-N-[1-[(6-chloro-3-pyridyl)methyl]-2-pyridylidene]-2,2,2-trifluoro-acetamide;

M.UN.6b) (E/Z)-N-[1-[(6-chloro-5-fluoro-3-pyridyl)methyl]-2-pyridylidene]-2,2,2-trifluoro-acetamide;

M.UN.6c) (E/Z)-2,2,2-trifluoro-N-[1-[(6-fluoro-3-pyridyl)methyl]-2-pyridylidene]acetamide;

M.UN.6d) (E/Z)-N-[1-[(6-bromo-3-pyridyl)methyl]-2-pyridylidene]-2,2,2-trifluoro-acetamide;

M.UN.6e) (E/Z)-N-[1-[1-(6-chloro-3-pyridyl)ethyl]-2-pyridylidene]-2,2,2-trifluoro-acetamide;

M.UN.6f) (E/Z)-N-[1-[(6-chloro-3-pyridyl)methyl]-2-pyridylidene]-2,2-difluoro-acetamide;

M.UN.6g) (E/Z)-2-chloro-N-[1-[(6-chloro-3-pyridyl)methyl]-2-pyridylidene]-2,2-difluoro-acetamide;

M.UN.6h) (E/Z)-N-[1-[(2-chloropyrimidin-5-yl)methyl]-2-pyridylidene]-2,2,2-trifluoro-acetamide;

M.UN.6i) (E/Z)-N-[1-[(6-chloro-3-pyridyl)methyl]-2-pyridylidene]-2,2,3,3,3-pentafluoro-propanamide.);

M.UN.6j) N-[1-[(6-chloro-3-pyridyl)methyl]-2-pyridylidene]-2,2,2-trifluoro-thioacetamide or of the compound M.UN.6k) N-[1-[(6-chloro-3-pyridyl)methyl]-2-pyridylidene]-2,2,2-trifluoro-N'-isopropyl-acetamidine or the compounds M.UN.8: 8-chloro-N-[2-chloro-5-methoxyphenyl)sulfonyl]-6-trifluoromethyl)-imidazo[1,2-a]pyridine-2-carboxamide; or M.UN.9: 4-[5-(3,5-dichlorophenyl)-5-(trifluoromethyl)-4H-isoxazol-3-yl]-2-methyl-N-(1-oxothietan-3-yl)benzamide; or M.UN.10: 5-[3-[2,6-dichloro-4-(3,3-dichloroallyloxy)phenoxy]propoxy]-1H-pyrazole; or a compound selected from the group of M.UN.11, wherein the compound is selected from M.UN.11a) to M.UN.11p):

M.UN.11.a) 3-[benzoyl(methyl)amino]-N-[2-bromo-4-[1,2,2,2-tetrafluoro-1-(trifluoromethyl)ethyl]-6-(trifluoromethyl)phenyl]-2-fluoro-benzamide;

M.UN.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide;

M.UN.11.c) 3-(benzoylmethylamino)-2-fluoro-N-[2-iodo-4-[1,2,2,2-tetrafluoro-1-(trifluoromethyl)ethyl]-6-(trifluoromethyl)phenyl]-benzamide;

M.UN.11.d) N-[3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.e) N-[3-[[[2-bromo-4-[1,2,2,2-tetrafluoro-1-(trifluoromethyl)ethyl]-6-(trifluoromethyl)phenyl]amino]carbonyl]-2-fluorophenyl]-4-fluoro-N-methyl-benzamide;

M.UN.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide;

M.UN.11.h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide;

M.UN.11.i) 4-cyano-N-[2-cyano-5-[[2,6-dibromo-4-[1,2,2,3,3,3-hexafluoro-1-(trifluoromethyl)propyl]phenyl]carbamoyl]phenyl]-2-methyl-benzamide;

M.UN.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide;

M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide;

M.UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide;

M.UN.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide;

M.UN.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide;

M.UN.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide;

M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or a compound selected from the group of M.UN.12, wherein the compound is selected from M.UN.12a) to M.UN.12m):

M.UN.12.a) 2-(1,3-Dioxan-2-yl)-6-[2-(3-pyridinyl)-5-thiazolyl]-pyridine;

M.UN.12.b) 2-[6-[2-(5-Fluoro-3-pyridinyl)-5-thiazolyl]-2-pyridinyl]-pyrimidine;

M.UN.12.c) 2-[6-[2-(3-Pyridinyl)-5-thiazolyl]-2-pyridinyl]-pyrimidine;

M.UN.12.d) N-Methylsulfonyl-6-[2-(3-pyridyl)thiazol-5-yl]pyridine-2-carboxamide

M.UN.12.e) N-Methylsulfonyl-6-[2-(3-pyridyl)thiazol-5-yl]pyridine-2-carboxamide

M.UN.12.f) N-Ethyl-N-[4-methyl-2-(3-pyridyl)thiazol-5-yl]-3-methylthio-propanamide M.UN.12.g) N-Methyl-N-[4-methyl-2-(3-pyridyl)thiazol-5-yl]-3-methylthio-propanamide M.UN.12.h) N,2-Dimethyl-N-[4-methyl-2-(3-pyridyl)thiazol-5-yl]-3-methylthio-propanamide M.UN.12.i) N-Ethyl-2-methyl-N-[4-methyl-2-(3-pyridyl)thiazol-5-yl]-3-methylthio-propanamide M.UN.12.j) N-[4-Chloro-2-(3-pyridyl)thiazol-5-yl]-N-ethyl-2-methyl-3-methylthio-propanamide M.UN.12.k) N-[4-Chloro-2-(3-pyridyl)thiazol-5-yl]-N,2-dimethyl-3-methylthio-propanamide M.UN.12.l) N-[4-Chloro-2-(3-pyridyl)thiazol-5-yl]-N-methyl-3-methylthio-propanamide M.UN.12.m) N-[4-Chloro-2-(3-pyridyl)thiazol-5-yl]-N-ethyl-3-methylthio-propanamide; or the compound M.UN.13: 2-(4-methoxyiminocyclohexyl)-2-(3,3,3-trifluoropropylsulfonyl)acetonitrile; or the compounds M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol; or the compound M.UN.15: 1-[(2-Chloro-1,3-thiazol-5-yl)methyl]-3-(3,5-dichlorophenyl)-9-methyl-4-oxo-4H-pyrido[1,2-a]pyrimidin-1-ium-2-olate.

The commercially available compounds of the group M listed above may be found in The Pesticide Manual, 15th Edition, C. D. S. Tomlin, British Crop Protection Council (2011) among other publications.

The neonicotinoid cycloxaprid is known from WO20120/069266 and WO2011/06946, and the neonicotinoid compound M.4A.2, sometimes also to be named as Guadipyr, is known from WO2013/003977, and the neonicotinoid compound M.4A.3. (approved as paichongding in China) is known from WO2010/069266. The Metaflumizone analogue M.22B.1 is described in CN 10171577 and the analogue M.22B.2 in CN102126994. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide compound M.28.5i) is described in WO2011/085575, the compound M.28.5j) in WO2008/134969, the compound M.28.5k) in US2011/046186 and the compound M.28.5l) in WO2012/034403. The diamide compounds M.28.6 and M.28.7 can be found in CN102613183. The anthranilamide compounds M.28.8a) and M.28.8b) are known from WO2010/069502.

The quinoline derivative flometoquin is shown in WO2006/013896. The aminofuranone compounds flupyradifurone is known from WO 2007/115644. The sulfoximine compound sulfoxaflor is known from WO2007/149134. From the pyrethroids group momfluorothrin is known from U.S. Pat. No. 6,908,945 and heptafluthrin from WO10133098. The oxadiazolone compound metoxadiazone can be found in JP13/166707. The pyrazole acaricide pyflubumide is known from WO2007/020986. The isoxazoline compounds have been described in following publications: fluralaner in WO2005/085216, afoxolaner in WO2009/002809 and in WO2011/149749 and the isoxazoline compound M.UN.9 in WO2013/050317. The pyripyropene derivative afidopyropen has been described in WO 2006/129714. The nematicide tioxazafen has been disclosed in WO09023721 and nematicide fluopyram in WO2008126922, nematicidal mixtures comprising flupyram in WO2010108616. The triflumezopyrim compound was described in WO2012/092115.

The spiroketal-substituted cyclic ketoenol derivative M.UN.3 is known from WO2006/089633 and the biphenyl-substituted spirocyclic ketoenol derivative M.UN.4 from WO2008/067911.

The triazoylphenylsulfide M.UN.5 has been described in WO2006/043635, and biological control agents on basis of *bacillus firmus* in WO2009/124707.

The compounds M.UN.6a) to M.UN.6i) listed under M.UN.6 have been described in WO2012/029672 and compounds M.UN.6j) and M.UN.6k) in WO2013129688. The nematicide compound M.UN.8 in WO2013/055584 and the Pyridalyl-type analogue M.UN.10 in WO2010/060379. The carboxamide compounds M.UN.11.a) to M.UN.11.h) can be prepared as described in WO 2010/018714 and the carboxamide M.UN.11i) to M.UN.11.p) are described WO2010/127926. The pyridylthiazoles M.UN.12.a) to M.UN.12.c) are known from WO2010/006713, M.UN.12.c) and M.UN.12.d) WO2012000896 and M.UN.12.f) to M.UN.12.m) in WO2010129497. The malononitrile compound M.UN.13 was described in WO2009/005110. The compounds M.UN.14a) and M.UN.14b) are known from WO2007/101369. The compound M.UN.15 can be found in WO13192035.

The following list F of active substances, in conjunction with which the compounds according to the invention can be used, is intended to illustrate the possible combinations but does not limit them:

F.I) Respiration Inhibitors

F.I-1) Inhibitors of complex III at Qo site:
strobilurins: azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, triclopyricarb/chlorodincarb, trifloxystrobin, 2-[2-(2,5-dimethyl-phenoxymethyl)-phenyl]-3-methoxy-acrylic acid methyl ester and 2 (2-(3-(2,6-dichlorophenyl)-1-methyl-allylideneaminooxymethyl)-phenyl)-2-methoxyimino-N methyl-acetamide;
oxazolidinediones and imidazolinones: famoxadone, fenamidone;

F.I-2) Inhibitors of complex II (e.g. carboxamides):
carboxanilides: benodanil, benzovindiflupyr, bixafen, boscalid, carboxin, fenfuram, fenhexamid, fluopyram, flutolanil, furametpyr, isopyrazam, isotianil, mepronil, oxycarboxin, penflufen, penthiopyrad, sedaxane, tecloftalam, thifluzamide, tiadinil, 2-amino-4 methyl-thiazole-5-carboxanilide, N-(3',4',5' trifluorobiphenyl-2 yl)-3-difluoromethyl-1-methyl-1H-pyrazole-4 carboxamide (fluxapyroxad), N-(4'-trifluoromethylthiobiphenyl-2-yl)-3 difluoromethyl-1-methyl-1H pyrazole-4-carboxamide, N-(2-(1,3,3-trimethyl-butyl)-phenyl)-1,3-dimethyl-5 fluoro-1H-pyrazole-4 carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl) pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

F.I-3) Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate, 3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;

F.I-4) Other respiration inhibitors (complex I, uncouplers) diflumetorim; (5,8-difluoro-quinazolin-4-yl)-{2-[2-fluoro-4-(4-trifluoromethylpyridin-2-yloxy)-phenyl]-ethyl}-amine; tec-nazen; ferimzone; ametoctradin; silthiofam; nitrophenyl derivates: binapacryl, dinobuton, di-nocap, fluazinam, nitrthal-isopropyl, and including organometal compounds: fentin salts, such as fentin-acetate, fentin chloride or fentin hydroxide;

F.II) Sterol biosynthesis inhibitors (SBI fungicides)

F.II-1) C14 demethylase inhibitors (DMI fungicides, e.g. triazoles, imidazoles)
triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, paclobutrazole, penconazole, propiconazole, prothioconazole, simeconazole, tebuconazole, tetraconazole, triad-imefon, triadimenol, triticonazole, uniconazole, 1-[rel-(2S3R)-3-(2-chlorophenyl)-2-(2,4-difluorophenyl)-oxiranylmethyl]-5-thiocyanato-1H-[1,2,4]triazole, 2-[rel-(2S; 3R)-3-(2-chlorophenyl)-2-(2,4-difluorophenyl)-oxiranylmethyl]-2H-[1,2,4]triazole-3-thiol; imidazoles: imazalil, pefurazoate, oxpoconazole, prochloraz, triflumizole;
pyrimidines, pyridines and piperazines: fenarimol, nuarimol, pyrifenox, triforine, 1-[rel-(2S; 3R)-3-(2-chlorophenyl)-2-(2,4-difluorophenyl)-oxiranylmethyl]-5-thiocyanato-1H-[1,2,4]triazole, 2-[rel-(2S; 3R)-3-(2-chlorophenyl)-2-(2,4-difluorophenyl)-oxiranylmethyl]-2H-[1,2,4]triazole-3-thiol;

F.II-2) Delta14-reductase inhitors (Amines, e.g. morpholines, piperidines)
morpholines: aldimorph, dodemorph, dodemorph-acetate, fenpropimorph, tridemorph; piperidines: fenpropidin, piperalin; spiroketalamines: spiroxamine;

F.II-3) Inhibitors of 3-keto reductase: hydroxyanilides: fenhexamid;

F.III) Nucleic acid synthesis inhibitors

F.III-1) RNA, DNA synthesis
phenylamides or acyl amino acid fungicides: benalaxyl, benalaxyl-M, kiralaxyl, metalaxyl, metalaxyl-M (mefenoxam), ofurace, oxadixyl;
isoxazoles and iosothiazolones: hymexazole, octhilinone;

F.III-2) DNA topisomerase inhibitors: oxolinic acid;

F.III-3) Nucleotide metabolism (e.g. adenosin-deaminase), hydroxy (2-amino)-pyrimidines: bupirimate;

F.IV) Inhibitors of cell division and or cytoskeleton

F.IV-1) Tubulin inhibitors: benzimidazoles and thiophanates: benomyl, carbendazim, fuberidazole, thiabendazole, thiophanate-methyl;
triazolopyrimidines: 5-chloro-7 (4-methylpiperidin-1-yl)-6-(2,4,6-trifluorophenyl)-[1,2,4]triazolo[1,5 a]pyrimidine;

F.IV-2) Other cell division inhibitors
benzamides and phenyl acetamides: diethofencarb, ethaboxam, pencycuron, fluopicolide, zoxamide;

F.IV-3) Actin inhibitors: benzophenones: metrafenone, pyriofenone;

F.V) Inhibitors of amino acid and protein synthesis

F.V-1) Methionine synthesis inhibitors (anilino-pyrimidines) anilino-pyrimidines: cyprodinil, mepanipyrim, nitrapyrin, pyrimethanil;

F.V-2) Protein synthesis inhibitors (anilino-pyrimidines)
antibiotics: blasticidin-S, kasugamycin, kasugamycin hydrochloride-hydrate, mildiomycin, streptomycin, oxytetracyclin, polyoxine, validamycin A;
F.VI) Signal transduction inhibitors
F.VI-1) MAP/Histidine kinase inhibitors (e.g. anilino-pyrimidines)
dicarboximides: fluoroimid, iprodione, procymidone, vinclozolin;
phenylpyrroles: fenpiclonil, fludioxonil;
F.VI-2) G protein inhibitors: quinolines: quinoxyfen;
F.VII) Lipid and membrane synthesis inhibitors
F.VII-1) Phospholipid biosynthesis inhibitors
organophosphorus compounds: edifenphos, iprobenfos, pyrazophos;
dithiolanes: isoprothiolane;
F.VII-2) Lipid peroxidation: aromatic hydrocarbons: dicloran, quintozene, tecnazene, tolclo-fos-methyl, biphenyl, chloroneb, etridiazole;
F.VII-3) Carboxyl acid amides (CAA fungicides)
cinnamic or mandelic acid amides: dimethomorph, flumorph, mandiproamid, pyrimorph; valinamide carbamates: benthiavalicarb, iprovalicarb, pyribencarb, valifenalate and N-(1-(1-(4-cyano-phenyl)ethanesulfonyl)-but-2-yl) carbamic acid-(4-fluorophenyl) ester;
F.VII-4) Compounds affecting cell membrane permeability and fatty acids:
1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, carbamates: propamocarb, propamocarb-hydrochlorid;
F.VII-5) fatty acid amide hydrolase inhibitors: 1-[4-[4-[5-(2,6-difluorophenyl)-4,5-dihydro-3-isoxazolyl]-2-thiazolyl]-1-piperid inyl]-2-[5-methyl-3-(trifluoromethyl)-1H-pyrazol-1-yl]ethanone;
F.VIII) Inhibitors with Multi Site Action
F.VIII-1) Inorganic active substances: Bordeaux mixture, copper acetate, copper hydroxide, copper oxychloride, basic copper sulfate, sulfur;
F.VIII-2) Thio- and dithiocarbamates: ferbam, mancozeb, maneb, metam, methasulphocarb, metiram, propineb, thiram, zineb, ziram;
F.VIII-3) Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
F.VIII-4) Guanidines and other: guanidine, dodine, dodine free base, guazatine, guazatine-acetate, iminoctadine, iminoctadine-triacetate, iminoctadine-tris(albesilate), 2,6-dimethyl-1 H,5H-[1,4]dithiino[2,3-c:5,6-c']dipyrrole-1,3,5,7(2H,6H)-tetraone;
F.VIII-5) Ahtraquinones: dithianon;
F.IX) Cell wall synthesis inhibitors
F.IX-1) Inhibitors of glucan synthesis: validamycin, polyoxin B;
F.IX-2) Melanin synthesis inhibitors: pyroquilon, tricyclazole, carpropamide, dicyclomet, fenoxanil;
F.X) Plant defense inducers
F.X-1) Salicylic acid pathway: acibenzolar-S-methyl;
F.X-2) Others: probenazole, isotianil, tiadinil, prohexadione-calcium;
phosphonates: fosetyl, fosetyl-aluminum, phosphorous acid and its salts;
F.XI) Unknown mode of action:bronopol, chinomethionat, cyflufenamid, cymoxanil, dazomet, debacarb, diclomezine, difenzoquat, difenzoquat-methylsulfate, diphenylamin, fenpyraza-mine, flumetover, flusulfamide, flutianil, methasulfocarb, nitrapyrin, nitrothal-isopropyl, oxa-thiapiprolin, oxin-copper, proquinazid, tebufloquin, tecloftalam, triazoxide, 2-butoxy-6-iodo-3-propyl-chromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2 methyl-4-(3-trimethylsilanyl-propoxy)-phenyl)-N-ethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, methoxy-acetic acid 6-tert-butyl-8-fluoro-2,3-dimethyl-quinolin-4-yl ester and N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-chloro-phenyl)-2,3-dimethyl-isoxazolidin-3 yl]-pyridine, pyrisoxazole, 5-amino-2-isopropyl-3-oxo-4-ortho-tolyl-2,3-dihydropyrazole-1 carbothioic acid S-allyl ester, N-(6-methoxy-pyridin-3-yl) cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide.

F.XI) Growth regulators: abscisic acid, amidochlor, ancymidol, 6-benzylaminopurine, brassinolide, butralin, chlormequat (chlormequat chloride), choline chloride, cyclanilide, da-minozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N 6-benzyladenine, paclobutrazol, prohexadione (prohexadione-calcium), prohydrojasmon, thidiazuron, triapen-thenol, tributyl phosphorotrithioate, 2,3,5 tri iodobenzoic acid, trinexapac-ethyl and uniconazole;

F.XII) Biological control agents
*Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BO-TECTOR® from bio-ferm GmbH, Germany), *Bacillus pumilus* (e.g. NRRL Accession No. B-30087 in SONATA® and BALLAD® Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCU RE® (in mixture with lysozyme) and BIOCOAT® from Micro Flo Company, USA (BASF SE) and Arysta), Chitosan (e.g. ARMOURZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CON-TANS® from Prophyta, Germany), *Cryphonectria parasitica* (e.g. *Endothia parasitica* from CNICM, France), *Cryptococcus*

*albidus* (e.g. YIELD PLUS® from Anchor Bio-Technologies, South Africa), *Fusarium oxysporum* (e.g. BIO-FOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-lnnovation AB, Sweden), *T. stromaticum* (e.g. TRICO-VAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy), *Ulocadium oudemansii* HRU3 (e.g. BOTRY-ZEN® from Botry-Zen Ltd, NZ). The animal pest, i.e. the insects, arachnids and nematodes, the plant, soil or water in which the plant is growing can be contacted with the present compounds of formula (I) or composition(s) containing them by any application method known in the art. As such, "contacting" includes both direct contact (applying the compounds/compositions directly on the animal pest or plant, typically to the foliage, stem or roots of the plant) and indirect contact (applying the compounds/compositions to the locus of the animal pest or plant).

The compounds of formula (I) or the pesticidal compositions comprising them may be used to protect growing plants and crops from attack or infestation by animal pests, especially insects, acaridae or arachnids by contacting the plant/crop with a pesticidally effective amount of compounds of formula (I). The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugar beet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the compound of formula (I). The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one compound of formula (I).

Moreover, animal pests may be controlled by contacting the target pest, its food supply, habitat, breeding ground or its locus with a pesticidally effective amount of compounds of formula (I). As such, the application may be carried out before or after the infection of the locus, growing crops, or harvested crops by the pest.

The compounds of the invention can also be applied preventively to places at which occurrence of the pests is expected.

The compounds of formula (I) may be also used to protect growing plants from attack or infestation by pests by contacting the plant with a pesticidally effective amount of compounds of formula (I). As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat Protoc. 2007; 2(5):1225-35, Curr Opin Chem Biol. 2006October; 10(5):487-91. Epub 2006 Aug. 28, Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e. g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e. g. WO 92/00377); glutamine synthetase (GS) inhibitors, such as glufosinate (see e. g. EP-A-0242236, EP-A-242246) or oxynil herbicides (see e. g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e. g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as a-endotoxins, e. g. CryIA(b), CryIA(c), CryIF, CryIF(a2), CryIIA(b), CryIIIA, Cry-IIIB(b1) or Cry9c; vegetative insecticidal proteins (VIP), e. g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomy-cetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are dis-closed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the mexican wild potato Solanum bulbocastanum) or T4-lyso-zym (e. g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e. g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e. g. Amflora® potato).

In general, "pesticidally effective amount" means the amount of active ingredient (here of compound of formula (I)) needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active ingredient per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula (I) are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitoes, crickets, or cockroaches. For use against said non-crop pests, compounds of formula (I) are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitoes, crickets etc. or cockroaches to eat it.

The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of formula (I) as aerosols (e.g. in spray cans), oil sprays or pump sprays are highly suitable for the non-professional user for controlling pests such as flies, fleas, ticks, mosquitos or cockroaches. Aerosol recipes are preferably composed of the active ingredient, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula (I) and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula (I) and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methyl-piperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula (I) and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula (I) are applied not only to the surrounding soil surface or into the under-floor soil in order to protect wooden materials but it can also be applied to lumbered articles such as surfaces of the under-floor concrete, alcove posts, beams, ply-woods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of formula (I) are also suitable for the treatment of seeds in order to protect the seed from insect pest, in particular from soil-living insect pests and the resulting plant s roots and shoots against soil pests and foliar insects.

The compounds of formula (I) are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedling's roots and shoots from insects, in particular from soil and foliar insects, said method comprising contacting the seeds before sowing and/or after pregermination with a compound of the general formula (I) or a salt thereof. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the compound of formula (I). The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugar beet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the compound of formula (I) may also be used for the treatment seeds from plants, which tolerate the action of herbicides or fungicides or insecticides owing to breeding, including genetic engineering methods.

For example, the compound of formula (I) can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the compound of formula (I) can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the compound of formula (I) is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter In a preferred embodiment a FS formulation is used for seed treatment. Typically, a FS formulation may comprise 1-800 g/l of active ingredient, 1-200 g/I Surfactant, 0 to 200 g/I anti-freezing agent, 0 to 400 g/l of binder, 0 to 200 g/l of a pigment and up to 1 liter of a solvent, preferably water.

Especially preferred FS formulations of compounds of formula (I) for seed treatment usually comprise from 0.1 to 80% by weight (1 to 800 g/I) of the active ingredient, from 0.1 to 20% by weight (1 to 200 g/I) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a fill-er/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula (I), or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed.

For specific crops such as lettuce the rate can be higher.

The compounds of formula (I) or the enantiomers or veterinary acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula (I) or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula (I) or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula (I) or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) are suitable for combating endo- and ectoparasites in and on animals.

Compounds of formula (I) or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula (I) or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula (I) or the enantiomers or veterinarily acceptable salts thereof and compositions comprising them are suitable for systemic and/or non-systemic control of ecto- and/or endoparasites. They are active against all or some stages of development.

The compounds of formula (I) are especially useful for combating ectoparasites.

The compounds of formula (I) are especially useful for combating parasites of the following orders and species (e.g. as above previously listed in the target pests if not explicitly listed hereunder), respectively:

fleas (Siphonaptera);
cockroaches (Blattaria-Blattodea);
flies, mosquitoes (Diptera);
lice (Phthiraptera);
ticks and parasitic mites (Parasitiformes) from arachnoidea;
Actinedida (Prostigmata) und Acaridida (Astigmata);
Bugs (Heteropterida);
Anoplurida, e.g. *Haematopinus* spp., *Linognathus* spp., *Pediculus* spp., *Phtirus* spp., and *Solenopotes* spp; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp;

Roundworms Nematoda, e.g. Wipeworms and Trichinosis (Trichosyringida), e.g. Trichinelli-dae (*Trichinella* spp.), (Trichuridae) *Trichuris* spp., *Capillaria* spp; Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus*, and *Dioctophyma renale;*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp;

Thorny headed worms (Acanthocephala), e.g. *Acanthocephalus* spp., *Macracanthorhynchus hirudinaceus* and *Oncicola* spp, Planarians (Plathelminthes):
Flukes (Trematoda), e.g. *Faciola* spp., *Fascioloides magna, Paragonimus* spp., *Dicrocoelium* spp., *Fasciolopsis*

*buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula (I) and compositions containing them are particularly useful for the control of pests from the orders Diptera, Siphonaptera and Ixodida.

Moreover, the use of the compounds of formula (I)formula (I) and compositions containing them for combating mosquitoes is especially preferred.

The use of the compounds of formula I and compositions containing them for combating flies is a further preferred embodiment of the present invention.

Furthermore, the use of the compounds of formula (I) and compositions containing them for combating fleas is especially preferred.

The use of the compounds of formula (I) and compositions containing them for combating ticks is a further preferred embodiment of the present invention.

The compounds of formula (I) also are especially useful for combating endoparasites (roundworms nematoda, thorny headed worms and planarians).

Administration can be carried out both prophylactically and therapeutically. Administration of the active component(s) is carried out directly or in the form of suitable preparations, orally, topically/dermally or parenterally. The term active component(s) as used above mean comprising at least one compound of formula (I) and eventually further active compound(s).

For oral administration to warm-blooded animals, the compounds of formula (I) may be formulated as animal feeds, animal feed premixes, animal feed concentrates, pills, solutions, pastes, suspensions, drenches, gels, tablets, boluses and capsules. In addition, the compounds of formula (I) may be administered to the animals in their drinking water. For oral administration, the dosage form chosen should provide the animal with 0.01 mg/kg to 100 mg/kg of animal body weight per day of the formula (I) compound, preferably with 0.5 mg/kg to 100 mg/kg of animal body weight per day.

Alternatively, the compounds of formula (I) may be administered to animals parenterally, for example, by intraruminal, intramuscular, intravenous or subcutaneous injection. The compounds of formula (I) may be dispersed or dissolved in a physiologically acceptable carrier for subcutaneous injection. Alternatively, the compounds of formula (I) may be formulated into an implant for subcutaneous administration. In addition the compound of formula (I) may be transdermally administered to animals. For parenteral administration, the dosage form chosen should provide the animal with 0.01 mg/kg to 100 mg/kg of animal body weight per day of the compound of formula (I).

The compounds of formula (I) may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the compound of formula (I). In addition, the compounds of formula (I) may be formulated as ear tags for animals, particularly quadrupeds such as cattle and sheep. Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active component is processed in an ointment base or in an oil-in-water or water-in-oil emulsion base;

Solid preparations such as powders, premixes or concentrates, granules, pellets, tablets, boluses, capsules; aerosols and inhalants, and active component containing shaped articles. Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active component(s) can optionally be dissolved in physiologically tolerable vegetable or synthetic oils which are suitable for injection.

Suitable solubilizers are solvents which promote the dissolution of the active component in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula (I).

Generally it is favorable to apply the compounds of formula (I) in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula (I) against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula (I) are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula (I) in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyam-ides and polyester which are sufficiently compatible with the compounds of formula (I). A detailed list of plastics and elastomers as well as preparation procedures for the shaped articles is given e.g. in WO 03/086075.

The present invention is now illustrated in further details by the following examples, without imposing any limitation thereto.

S. SYNTHESIS EXAMPLES

Example. 1

Synthesis S1

2-[6-Chloro-3-pyridyl]-3H-5a-aza-2a-azonaacenaph-thylene, 4,5-dihydro-3,5-dioxo-4-phenyl-, inner salt

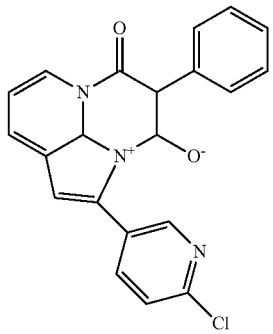 [SMILES: O=C1C(c2ccccc2)C([O-])[NH+]2C(c3ccc(Cl)nc3)=CC3=CC=CN1C32]

Step 1: 2-(6-chloro-3-pyridyl)-1H-pyrrolo[2,3-b]pyridine 1.56 g (10 mmol) 1-(6-chloro-3-pyridinyl)-1-ethanone was dissolved in 5 ml THF and 2 eq. of a solution of sodium hexamethyldisilazane in THF was added under Argon and stirred for 5 minutes. 0.43 g (2.5 mmol) of 2-amino-3-bromopyridine together with 0.29 g (0.5 mmol) Pd(dba)$_2$ were dissolved in 5 ml THF and added. After five more minutes of stirring, 0.29 g (1 mmol) tri-tert-butylphospine tetrafluoro borate was added and the mixture was kept under gentle reflux for 3 d. After addition of ethyl acetate the solid residues were filtered off and the solution was extracted with water and dried over magnesium sulfate. After removal of the solvent, the residue was taken up in methylene chloride and filtered. This yielded 63 mg of the desired product, which was used in the next step.

Step 2: 2-[6-Chloro-3-pyridyl]-3H-5a-aza-2a-azoni-aacenaphthylene 4,5-dihydro-3,5-dioxo-4-phenyl-, inner salt The product from step 1 (63 mg, 0.27 mmol) and bis(2, 4,6-trichlorophenyl) 2-phenylpropanedioate (250 mg, 0.46 mmol) was taken up in bromobenzene (5 ml) and heated to 185° C. for ten minutes. The solvent was removed to give the crude material. Purification by column chromatography yielded the pure product (17 mg, yield: 17%).

$^1$H NMR (400 MHz, D6-DMSO): δ 9.21 (d, 1H), 8.88 (d, 1H), 8.72 (s, 1H), 8.19 (d, 1H), 7.92 (t, 1H), 7.63~7.18 (m, 7H).

Compounds can in general be characterized e.g. by coupled High Performance Liquid Chromatography/mass spectrometry (HPLC/MS), by $^1$H-NMR and/or by their melting points.

Conditions:

Analytical HPLC column 1: RP-18 column Chromolith Speed ROD from Merck KgaA, Germany). Elution: acetonitrile+0.1% trifluoroacetic acid (TFA)/water+0.1% trifluoroacetic acid (TFA) in a ratio from 5:95 to 95:5 in 5 minutes at 40° C.

r.t.=HPLC retention time (RT) in minutes; m/z of the [M+H]+, [M+Na]+ or [M+K]+ peaks.

Analytical HPLC column 2: Phenomenex Kinetex 1.7 μm XB-C18 100A; 50×2.1 mm

Elution: A: acetonitrile+0.1% trifluoroacetic acid (TFA)/water+0.1% trifluoroacetic acid (TFA) in a ratio of from 5:95 to 95:5 in 1.5 minutes at 50° C.

MS-method: ESI positive.

$^1$H-NMR, respectively $^{13}$C-NMR: The signals are characterized by chemical shift δ (ppm) vs. tetramethylsilane, respectively CDCl$_3$ for $^{13}$C-NMR, by their multiplicity and by their integral (relative number of hydrogen atoms given). The following abbreviations are used to charac-terize the multiplicity of the signals: m=multiplett, q=quartett, t=triplett, d=doublet and s=singulett. The coupling constant (J) is expressed in Hertz (Hz).

Further compounds examples of the present invention were prepared by analogy to the above described synthetic methods and the hereunder table illustrates, without imposing any limitation thereto, compounds examples of formula (I) including their corresponding characterization data:

| N° | Formula | Characterization ¹H-NMR and/or HPLC/MS δ (ppm); J (Hz) |
|---|---|---|
| C-1 | | LC-MS RT 0.966 min m/z 374, 1 H-NMR (DMSO/ppm) 9.25 (d, 1H), 8.90 (d, 1H), 8.70 (s, 1H), 8.20 (dd, 1H), 7.95 (t, 1H), 7.65 (d, 1H), 7.60 (d, 2H), 7.35 d, 1H), 7.30 (d, 2H), 7.15 (t, 1H) |
| C-2 | | LC-MS RT 0.706 min m/z 386, 1 H-NMR (DMSO/ppm/400 MHz) 7.66-7.58 (m, 2H), 7.24 (q, 2H), 7.10-7.09 (m, 1H), 5.94-5.88 (m, 1H), 4.22-4.13 (m, 1H), 3.84-3.77 (m, 1H), 3.58-3.56 (m, 1H), 3.45-3.25 (m, 2H), 2.45-2.40 (m, 2H), 2.32-2.29 (m, 2H), 2.13-2.10 (m, 1H) |
| C-3 | | LC/MS RT 0.697 min m/z 386, 1 H-NMR (CDCl3/ppm/400 MHz) 7.68 (d, 2H), 7.60 (s, 1H), 7.36 (t, 2H), 7.21 (t, 1H), 5.99 (d, 1H), 4.23 (q, 1H), 3.72-3.68 (m, 1H), 3.57-3.54 (m, 1H), 2.93-2.88 (q, 1H), 2.50 (q, 1H), 2.42-2.39 (m, 2H), 1.99-1.87 (m, 1H), 1.59 (q, 1H) |
| C-4 | | LC-MS RT 0.706 min m/z 386, 1 H-NMR (DMSO/ppm/400 MHz) 7.66-7.58 (m, 2H), 7.24 (q, 2H), 7.21-7.09 (m, 1H), 5.94-5.88 (m, 1H), 4.22-4.13 (m, 1H), 3.84-3.77 (m, 1H), 3.58-3.57 (m, 1H), 3.45-3.25 (m, 2H), 2.60-2.40 (m, 2H), 2.32-2.29 (m, 2H), 2.13-1.99 (m, 1H) |
| C-5 | | LC-MS RT 1.128 min m/z 442.5 H-NMR (CDCl3/ppm) 9.35 (d, 1H), 8.65 (s, 1H), 8.60 (d, 1H), 8.10 (dd, 1H), 8.00 (s, 1H), 7.85 (t, 1H), 7.80 (t, 1H), 7.50 (d, 2H), 7.40 (d, 1H), 7.00 (s, 1H) |
| C-6 | | LC/MS RT 0.792 min m/z 400, 1H-NMR (DMSO/ppm/400 MHz) 7.63 (q, 2H), 7.25 (q, 2H), 7.11 (q, 1H), 6.14 (s, 1H), 4.82-4.79 (m, 1H), 4.14-4.09 (m, 1H), 3.77-3.74 (m, 1H), 3.35-3.25-(m, 1H), 3.10-2.99 (m, 1H), 2.40-2.15 (m, 3H), 2.06-2.02 (m, 1H), 1.83-1.54 (m, 3H) |
| C-7 | | H-NMR (MeOD/ppm/400 MHz) 7.572 (s, 1H), 7.47 (d, 2H), 7.29 (t, 2H), 7.15 (t, 1H), 6.41 (s, 1H), 4.57 (q, 1H), 3.64-3.56 (m, 5H), 2.56 (d (1H), 2.45-2.43 (m, 1H), 2.26-2.21 (m, 1H), 2.09-2.08 (m, 1H) |
| C-8 | | LC-MS RT 0.734 m/z 396.0 H-NMR (CDCl3/ppm/400 MHz) 9.46 (d, 1H), 7.90 (d, 1H), 7.76 (d, 2H), 7.39 (t, 2H), 7.35 (t, 1H), 7.33 (s, 1H), 7.27 (t, 1H), 6.69 (s, 1H), 3.24-3.16 (m, 2H), 2.64-2.57 (m, 1H), 2.38-2.29 (m, 1H) |

| N° | Formula | Characterization ¹H-NMR and/or HPLC/MS δ (ppm); J (Hz) |
|---|---|---|
| C-9 | | m/z = 464, 3 g/mol Rt = 1.137 min |
| C-10 | | m/z = 466, 1 g/mol Rt = 1.219 min |
| C-11 | | m/z = 425, 8 g/mol Rt = 0.937 min |
| C-12 | | m/z = 468, 8 g/mol Rt = 1.076 min |
| C-13 | | m/z = 468, 8 g/mol Rt = 1.006 min |
| C-14 | | m/z = 431, 2 g/mol Rt = 0.808 min |
| C-15 | | m/z = 454, 8 g/mol Rt = 0.959 min |
| C-16 | | m/z = 454, 8 g/mol Rt = 1.025 min |

The biological activity of the compounds of formula (I) of the present invention can be evaluated in biological tests as described in the following.

General conditions: If not otherwise specified, most test solutions are to be prepared as fol-lows:

The active compound is dissolved at the desired concentration in a mixture of 1:1 (vol:vol) distilled water: acetone. The test solution is prepared at the day of use.

Test solutions are prepared in general at concentrations of 2500 ppm, 1000 ppm, 500 ppm, 300 ppm, 100 ppm and 30 ppm (wt/vol).

Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 25±1° C. and about 75±5% relative humidity for 5 days. Egg and larval mortality was then visually assessed.

In this test, compounds C-7 and C-8 at 2500 ppm showed over 75% mortality in comparison with untreated controls.

Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, compounds C-2, C-6, C-3, C-7, C-4, C-8, C-9 and C-11 at 2500 ppm showed over 75% mortality in comparison with untreated controls.

Orchid *Thrips* (*Dichromothrips Corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus 0.01% vol/vol Alkamuls® EL 620 surfactant. *Thrips* potency of each compound was evaluated by using a floral-immersion technique. Plastic petri dishes were used as test arenas. All petals of individual, intact orchid flowers were dipped into treatment solution and allowed to dry. Treated flowers were placed into individual petri dishes along with about 20 adult *thrips*. The petri dishes were then covered with lids. All test arenas were held under continuous light and a temperature of about 28° C. for duration of the assay. After 3 days, the numbers of live *thrips* were counted on each flower, and along inner walls of each petri dish. The percent mortality was recorded 72 hours after treatment.

In this test, compounds C-2, C-6, C-3, C-7, C-4 and C-8 at 500 ppm showed over 75% mortality in comparison with untreated controls.

Rice Green Leafhopper (*Nephotettix virescens*)

Rice seedlings were cleaned and washed 24 hours before spraying. The active compounds were formulated in 50:50 acetone:water (vol:vol), and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compounds C-2, C-6, C-3, C-7, C-4 and C-8 at 500 ppm showed over 75% mortality in comparison with untreated controls.

Rice Brown Plant Hopper (*Nilaparvata lugens*)

Rice seedlings were cleaned and washed 24 hours before spraying. The active compounds were formulated in 50:50 acetone:water (vol:vol) and 0.1% vol/vol surfactant (EL 620) was added. Potted rice seedlings were sprayed with 5 ml test solution, air dried, placed in cages and inoculated with 10 adults. Treated rice plants were kept at about 28-29° C. and relative humidity of about 50-60%. Percent mortality was recorded after 72 hours.

In this test, compounds C-2, C-3, C-6, C-7 and C-8 at 500 ppm showed over 75% mortality in comparison with untreated controls.

Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, compounds C-8, C-9, C-10 and C-11 at 2500 ppm showed over 75% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, compounds C-2, C-6, C-3, C-7, C-8, C-9, C-10 and C-11 at 2500 ppm showed over 75% mortality in comparison with untreated controls.

The invention claimed is:

1. A substituted pyrimidinium compound of formula (I)

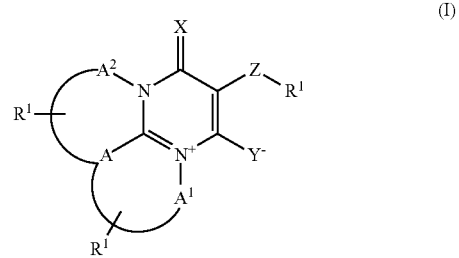

wherein

X, Y are O;

Z is a direct bond;

A is selected from the group consisting of C and N and, wherein the two nitrogens of the pyrimidinium ring taken together with the contiguous linking carbon atom and with A, $A^1$, and $A^2$ as depicted in formula (I), form an eight- to fourteen-membered bicyclic rings system which is substituted by at least one $R^1$ being not H, and wherein each remaining ring member of the bicyclic rings system is selected from carbon atoms and up to 4 heteroatoms independently selected from the group consisting of up to 2 O, up to 2 S, and up to 3 $N(R^c)_p$ in each ring, wherein the sulfur atom ring members are independently selected from $S(=O)_m$, wherein each ring may be partially or fully substituted by $R^1$; or two geminally bound groups $R^1$ together may form a group selected from the group consisting of =O, =S, =$CR^bR^c$, =$NR^c$, =$NOR^c$, and =$NNR^cR^c$;

$A^1$, $A^2$ are each independently selected from the group consisting of C and $CR^1$;

$R^1$ is each independently selected from the group consisting of hydrogen, D-2, D-9, D-13, D-17, D-22, D-25, D-28, D-29 and D-54:

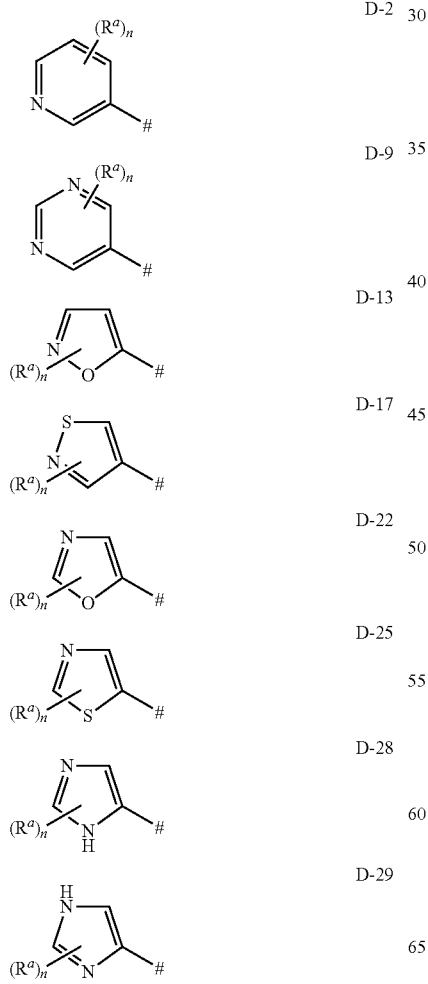

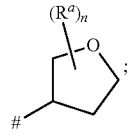

$R^a$ is each independently selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^c)R^b$, $ON=CR^bR^c$, $ONR^bR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, $N=S(=O)_pR^cR^c$, and a three- to six-membered saturated, or partially unsaturated or aromatic carbo- or heterocyclic ring, which may contain 1 to 3 heteroatoms selected from the group consisting of N—$(R^c)_p$, O, and S, wherein S may be oxidized, and wherein the aforementioned groups and the carbo- or heterocyclic ring may be partially or fully substituted by $R^{1aa}$; or two geminally bound groups $R^a$ together may form a group selected from the group consisting of =O, =S, =$CR^bR^c$, =$NR^c$, =$NOR^c$, and =$NNR^cR^c$;

$R^{1aa}$ is each independently selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $SO_2NR^b(=O)NR^bR^c$, $P(=X^2)R^bR^c$, $OP(=X^2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, and $N=S(=O)_pR^cR^c$, or two geminally bound groups $R^{1aa}$ together may form a group selected from the group consisting of =O, =S, =$CR^bR^c$, =$NR^c$, =$NOR^c$, and =$NNR^cR^c$;

$X^2$ is independently O or S;

$R^b$ is each independently selected from the group consisting of hydrogen, $C_1$-$C_6$-alkyl, $C_1$-$C_6$-haloalkyl, $C_1$-$C_6$-alkoxy, $C_1$-$C_6$-haloalkoxy and a three- to six-membered saturated, or partially unsaturated or aromatic carbo- or heterocyclic ring, which may contain 1 to 3 heteroatoms selected from the group consisting of $N(R^c)_p$, O, and S, wherein S may be oxidized and which carbo- or heterocyclic ring may be partially or fully substituted by $R^{aa}$;

$R^{aa}$ is each independently selected from the group consisting of halogen, $C_1$-$C_6$-alkyl, $C_1$-$C_6$-haloalkyl, $C_1$-$C_6$-alkoxy and $C_1$-$C_6$-haloalkoxy;

$R^c$ is each independently selected from the group consisting of hydrogen, $C_1$-$C_4$-alkyl, $C_1$-$C_4$-haloalkyl, $C_1$-$C_4$-alkylcarbonyl, $C_1$-$C_6$ cycloalkyl, and a three- to six-membered saturated, partially unsaturated or aromatic carbo- or heterocyclic ring, which may contain 1 to 3 heteroatoms selected from the group consisting of $N(R^{aa})_p$, O and S, wherein S may be oxidized and wherein the carbo- or heterocyclic ring may be partially or fully substituted by $R^{aa}$;

wherein two geminally bound groups $R^bR^b$, $R^cR^b$ or $R^cR^c$ together with the atom to which they are bound, may form a 3-, 4-, 5-, 6- or 7- membered saturated, partially unsaturated or aromatic carbo- or heterocyclic ring, which may contain 1 to 2 heteroatoms or heteroatoms groups selected from the group consisting of N, O, S, NO, SO and $SO_2$ and wherein the carbo- or heterocyclic ring may be partially or fully substituted by $R^3$;

$R^d$ is each independently selected from the group consisting of hydrogen, phenyl, $C_1$-$C_6$-alkyl, $C_2$-$C_6$-alkenyl, $C_2$-$C_6$-alkynyl, $C_3$-$C_8$-cycloalkyl, and $C_1$-$C_6$-alkoxyalkyl, wherein the above mentioned groups may be substituted by one or more halogen;

$R^e$ is each independently selected from the group consisting of $C_1$-$C_4$-alkyl, $C_1$-$C_4$-haloalkyl, $C_1$-$C_4$-alkylcarbonyl, $C_1$-$C_6$ cycloalkyl, and a three- to six-membered saturated, partially unsaturated or aromatic carbo- or heterocyclic ring, which may contain 1 to 3 heteroatoms selected from the group consisting of $N(R^{aa})_p$, O and S, wherein S may be oxidized and wherein the carbo- or heterocyclic ring may be partially or fully substituted by $R^{aa}$;

n is 0, 1 or 2;
m is 0, 1, or 2;
p is 0 or 1;

wherein at least one $R^1$ being not hydrogen is the substituent of the carbon atom adjacent to one nitrogen of the pyrimidinium ring;

$R^2$ is a six membered carbo- or heterocyclic ring, which ring may be unsubstituted, partially, or fully substituted by $R^{2a}$, and wherein $R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which groups may be substituted by halogen, $C_1$-$C_6$-haloalkyl or $C_1$-$C_6$-haloalkoxy;

$R^{2a}$ is each independently selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^e$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $SO_2NR^b(=O)NR^bR^c$, $P(=X^2)R^bR^c$, $OP(=X_2)(O_pR^c)R^b$, $OP(=X^2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^b$-$NR^bC(=X^2)NR^bR^c$, $NR^bNR^bSO_2NR^bR^c$, and $N=S(=O)_p$ $R^cR^c$, or two geminally bound groups $R^{2aa}$ together may form a group selected from the group consisting of =O, =S, $=CR^bR^c$, $=NR^c$, $=NOR^c$, and $=NNR^cR^c$;$R^3$ is each independently selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $SO_2NR^b(=O)NR^bR^c$, $P(=X^2)R^bR^c$, $OP(=X_2)(O_pR^c)R^b$, $OP(=X_2)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=X^2)NR^bR^c$, $NR^bNR^bSO_2NR^bR^c$, $N=S(=O)_pR^cR^c$, or two geminally bound groups $R^3$ together may form a group selected from the group consisting of =O, =S, $=CR^bR^c$, $=NR^c$, $=NOR^c$, and $=NNR^cR^c$;

and/or stereoisomers or agriculturally or veterinary acceptable salts or tautomers or N-oxides thereof.

2. The compound of formula (I) of claim 1, wherein A is C or N, and wherein the two nitrogens of the pyrimidinium ring taken together with the contiguous linking carbon atom, and with A, $A^1$, and $A^2$ as depicted in formula (I), form a nine- to ten-membered bicyclic rings system being a five- and a six-membered rings, wherein each remaining ring member of the bicyclic ring system is selected from carbon atoms and up to 3 heteroatoms independently selected from the group consisting of up to 2 O, up to 2 S, and up to 3 $N(R^c)_p$ in each ring, wherein the sulfur atom ring members are independently selected from $S(=O)_m$, wherein each ring may be partially or fully substituted by $R^1$; or two geminally bound groups $R^1$ together may form a group selected from the group consisting of =O, =S, $=CR^bR^c$, $=NOR^c$, and $=NNR^cR^c$.

3. The compound of formula (I) of claim 1, wherein A is C, and wherein A, A1, A2 and the pyrimidinium ring form a tricyclic ring system selected from the formulae (II-1) to (II-7):

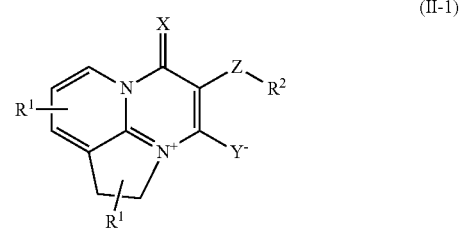

(II-1)

-continued

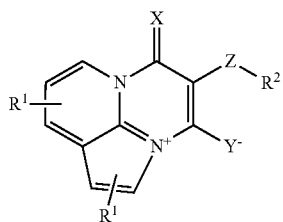
(II-2)

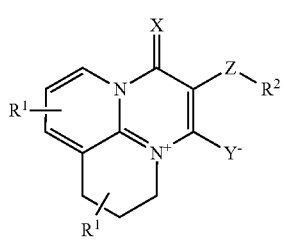
(II-3)

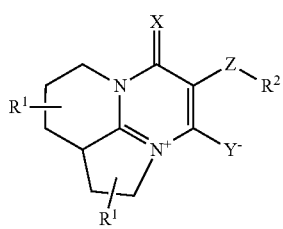
(II-4)

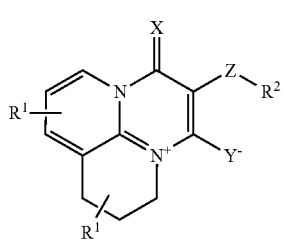
(II-5)

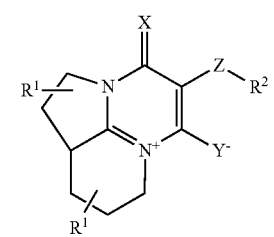
(II-6)

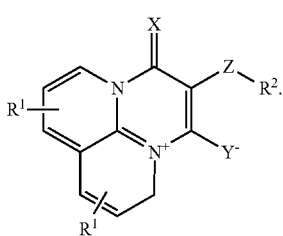
(II-7)

4. The compound of formula (I) of claim 1, wherein R¹ is selected from the hereunder mentioned structures D-2, D-9, D-22 D-25, D-28, D-29 and D-54:

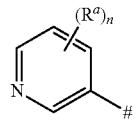
D-2

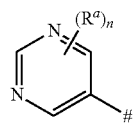
D-9

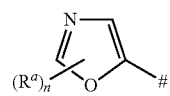
D-22

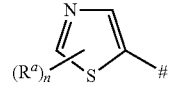
D-25

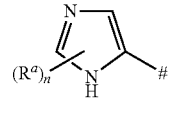
D-28

D-29

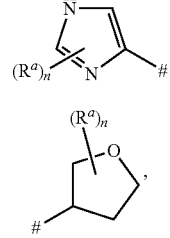
D-54 wherein $R^a$ is halogen or $C_1$-$C_4$-haloalkyl, n is 0, 1 or 2, and wherever used in a structure, the following:

\# denotes the bond to A in formula (I).

5. The compound of formula (I) of claim 3, wherein

A is C, and wherein A, A1, A2 and the pyrimidinium ring form a tricyclic ring system of the formula (II-1), (II-2) or (II-3);

R¹ is D-2, D-9 or D-25;

R² is phenyl which may be substituted by halogen, $C_1$-$C_6$-haloalkyl or $C_1$-$C_6$-haloalkoxy;

$R^a$ is Cl, Br, F, or CF₃.

6. The compound of formula (I) of claim 1, wherein R¹ is D-2, D-9, D-13, or D-17:

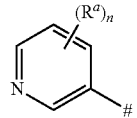
D-2

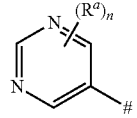
D-9

-continued

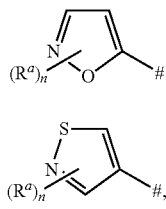

D-13

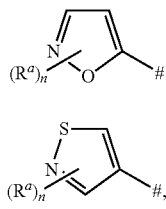

D-17 wherein $R^a$ is halogen or $C_1$-$C_4$-haloalkyl, n is 0, 1 or 2, and wherever used in a structure, the following:

\# denotes the bond to A in formula (I).

7. The compound of formula (I) of claim 1, wherein $R^1$ is D-22, D-25, or D-28:

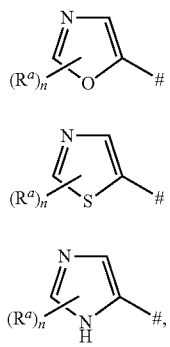

D-22

D-25

D-28 wherein $R^a$ is halogen or $C_1$-$C_4$-haloalkyl, n is 0, 1 or 2, and wherever used in a structure, the following:

\# denotes the bond to A in formula (I).

8. The compound of formula (I) of claim 7, wherein $R^1$ is D-2 or D-9:

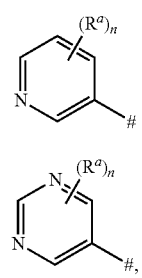

D-2

D-9 wherein $R^a$ is halogen or $C_1$-$C_4$-haloalkyl, n is 0, 1 or 2, and wherever used in a structure, the following:

\# denotes the bond to A in formula (I).

9. The compound of formula (I) of claim 7, wherein le is D-22 or D-25:

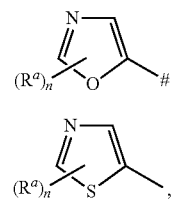

D-22

D-25 wherein $R^a$ is halogen or $C_1$-$C_4$-haloalkyl, n is 0, 1 or 2, and wherever used in a structure, the following:

\# denotes the bond to A in formula (I).

10. A composition comprising at least one compound of formula (I) as defined in claim 1, and at least one inert liquid and/or solid carrier.

11. An agricultural composition for combating animal pests comprising at least one compound of formula (I) as defined in claim 1, and at least one inert liquid and/or solid acceptable carrier and, if desired, at least one surfactant.

12. A method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing with a pesticidally effective amount of at least one compound of formula (I) as defined in claim 1.

13. A method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing with a pesticidally effective amount of the composition of claim 10.

14. A method for combating, controlling or protecting against infestation or infection by invertebrates pest, which method comprises contacting said pest or its food supply, habitat or breeding grounds with a pesticidally effective amount of at least one compound as defined in claim 1.

15. A method for combating, controlling or protecting against infestation or infection by invertebrates pest, which method comprises contacting said pest or its food supply, habitat or breeding grounds with a pesticidally effective amount of the composition of claim 10.

16. A non-therapeutic method for treating animals infested or infected by parasites or protecting animals against infestation or infection by parasites which comprises orally, topically or parenterally administering or applying to the animals a parasiticidally effective amount of the compound of claim 1.

17. A seed comprising the compound of claim 1, or the enantiomers, diastereomers or salts thereof, in an amount of from 0.1 g to 10 kg per 100 kg of seed.

18. The method of claim 12, wherein, in the compound of formula (I), A is C or N, and wherein the two nitrogens of the pyrimidinium ring taken together with the contiguous linking carbon atom, and with A, $A^1$, and $A^2$ as depicted in formula (I), form a nine- to ten-membered bicyclic rings system being a five- and a six-membered rings, wherein each remaining ring member of the bicyclic ring system is selected from carbon atoms and up to 3 heteroatoms independently selected from the group consisting of up to 2 O, up to 2 S, and up to 3 N($R^c$)$_p$ in each ring, wherein the sulfur atom ring members are independently selected from S(=O)$_m$, wherein each ring may be partially or fully substituted by $R^1$; or two geminally bound groups $R^1$ together may form a group selected from the group consisting of =O, =S, =CR$^b$R$^c$, =NR$^c$, =NOR$^c$, and =NNR$^c$R$^c$.

19. The method of claim 12, wherein, in the compound of formula (I), A is C, and wherein A, A1, A2 and the pyrimidinium ring form a tricyclic ring system selected from the formulae (II-1) to (II-7):

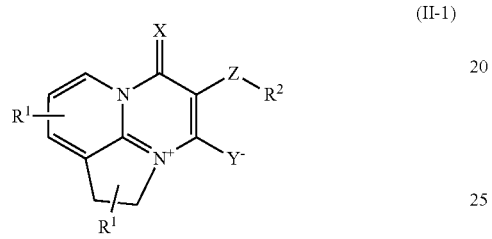
(II-1)

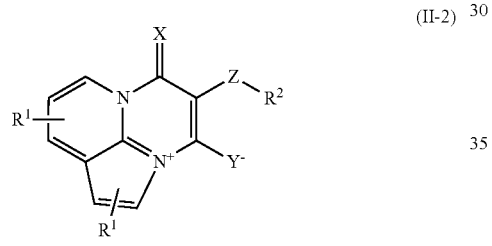
(II-2)

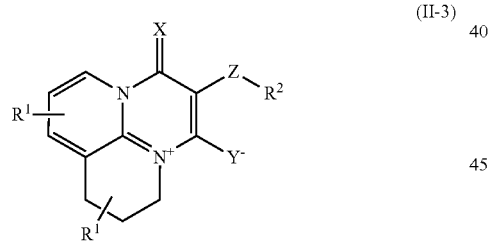
(II-3)

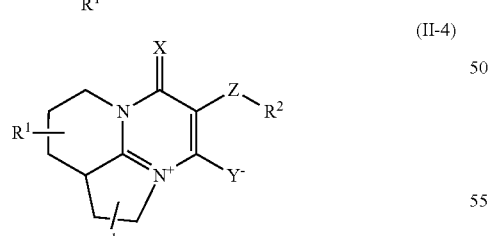
(II-4)

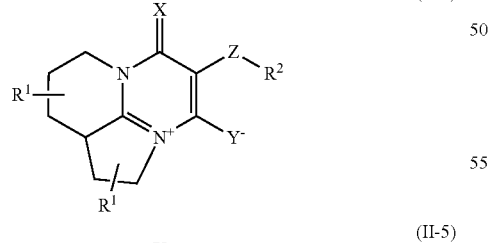
(II-5)

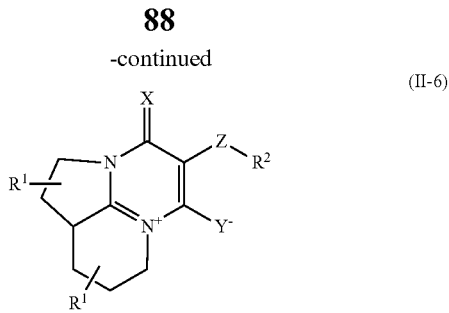
(II-6)

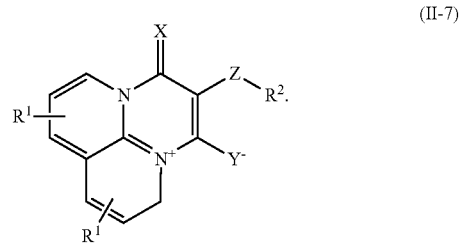
(II-7)

20. The method of claim 12, wherein, in the compound of formula (I), $R^1$ is selected from the hereunder mentioned structures D-2, D-9, D-22, D-25, D-28, D-29 and D-54:

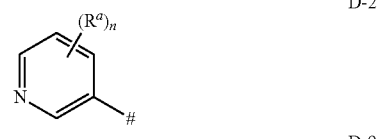
D-2

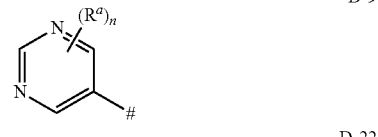
D-9

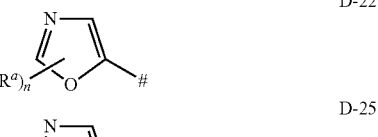
D-22

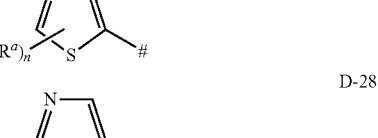
D-25

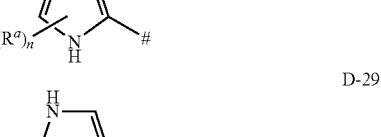
D-28

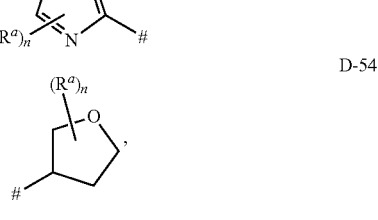
D-29

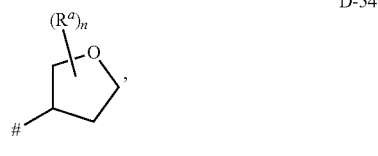
D-54 wherein
R$^a$ is halogen or C$_1$-C$_4$-haloalkyl,
n is 0, 1 or 2, and wherever used in a structure, the following:
# denotes the bond to A in formula (I).

21. The method of claim 12, wherein, in the compound of formula (I),
A is C, and wherein A, A1, A2 and the pyrimidinium ring form a tricyclic ring system of the formula (II-1), (II-2) or (II-3);
R$^1$ is D-2, D-9 or D-25;
R$^2$ is phenyl which may be substituted by halogen, C$_1$-C$_6$-haloalkyl or C$_1$-C$_6$-haloalkoxy;
R$^a$ is Cl, Br, F, or CF$_3$.

* * * * *